United States Patent
Som et al.

(10) Patent No.: US 10,639,327 B1
(45) Date of Patent: May 5, 2020

(54) NANO-CALCIUM CARBONATE

(71) Applicant: Washington University in St. Louis, St. Louis, MO (US)

(72) Inventors: Avik Som, Houston, TX (US); Samuel I. Achilefu, St. Louis, MO (US); Ramesh Raliya, St. Louis, MO (US); Pratim Biswas, Chesterfield, MO (US)

(73) Assignee: Washington University, Saint Louis, MO (US)

( * ) Notice: Subject to any disclaimer, the term of this patent is extended or adjusted under 35 U.S.C. 154(b) by 0 days.

(21) Appl. No.: 15/357,190

(22) Filed: Nov. 21, 2016

Related U.S. Application Data

(60) Provisional application No. 62/257,878, filed on Nov. 20, 2015.

(51) Int. Cl.
| | | |
|---|---|---|
| *A61K 9/51* | (2006.01) | |
| *A61K 33/10* | (2006.01) | |
| *C01F 11/18* | (2006.01) | |
| *A61K 47/42* | (2017.01) | |
| *A61K 49/00* | (2006.01) | |
| *A61K 45/06* | (2006.01) | |
| *A61K 47/48* | (2006.01) | |

(52) U.S. Cl.
CPC ............ *A61K 33/10* (2013.01); *A61K 9/5115* (2013.01); *A61K 45/06* (2013.01); *A61K 47/42* (2013.01); *A61K 47/48246* (2013.01); *A61K 47/48861* (2013.01); *A61K 49/0021* (2013.01); *C01F 11/18* (2013.01); *C01F 11/185* (2013.01); *C01P 2004/62* (2013.01); *C01P 2004/64* (2013.01); *C01P 2004/80* (2013.01)

(58) Field of Classification Search
CPC . A61K 9/001; A61K 9/14; A61K 9/51; A61K 9/5107; A61K 9/5115; A61K 9/5123; A61K 9/5161; A61K 47/50
See application file for complete search history.

(56) References Cited

U.S. PATENT DOCUMENTS

| | | |
|---|---|---|
| 6,762,052 B1 | 7/2004 | Cashman et al. |
| 8,076,451 B2 | 12/2011 | Reshetnyak et al. |
| 2011/0064750 A1 | 3/2011 | Fahim et al. |
| 2011/0104052 A1* | 5/2011 | Barnett ............... A61K 9/0019 424/1.21 |
| 2011/0177231 A1* | 7/2011 | Grinberg ............. A61K 9/0009 427/2.14 |
| 2011/0182918 A1 | 7/2011 | Kalnik et al. |
| 2014/0193837 A1* | 7/2014 | Zheng ............. G01N 33/54346 435/7.23 |

OTHER PUBLICATIONS

Tang et al, Induction of pH sensitivity on the fluorescence lifetime of quantum dots by NIR florescent dyes, Mar. 14, 2012, J Am Chem Soc, 134 (1), 4545-4548 (Year: 2012).*
Tang et al (Induction of pH Sensitivity on the fluorescence lifetime of quantum dots by NIR fluorescent dyes, J Am Chem Soc, Mar. 14, 2012:134; 10, pp. 45454-4548) (Year: 2012).*
Tang et al (US Induction of pH Sensitivity on the Fluorescence lifetime of quantum dots by NIR fluorescence dyes, J Am Chem Soc, Mar. 14, 2012:134; 10 pages 4545-4548). (Year: 2012).*
Katchamart, et al., Concurrent Flavin-Containing Monooxygenase Down-Regulation and Cytochrome P-450 Induction by Dietary Indoles in Rat: Implications for Drug-Drug Interation, vol. 28, No. 8, Drug Metabolism and Disposition, The American Society for Pharmacology and Experimental Therapeutics, pp. 931-936.
Reed, et al., Single-Dose and Multiple-Dose Administration of Indole-3-Carbinol to Women: Pharmacokinetics Based on 3,3'-Diindolylmethane, American Association for Cancer, 2006, pp. 2477-2481.
Weerakkody, et al., Family of pH (low) insertion peptides for tumor targeting, PNAS, vol. 110, No. 15, 2013, pp. 5834-5839.

* cited by examiner

*Primary Examiner* — Micah Paul Young
(74) *Attorney, Agent, or Firm* — Stinson LLP

(57) ABSTRACT

Disclosed are compositions comprising calcium carbonate nanoparticles and albumin. Also disclosed are compositions wherein the calcium carbonate nanoparticles further comprise targeting ligands, coatings, therapeutic agents and dyes. The compositions can be used in methods for neutralizing extracellular pH and in treating cancer.

7 Claims, 16 Drawing Sheets
(16 of 16 Drawing Sheet(s) Filed in Color)
Specification includes a Sequence Listing.

FIG. 1A
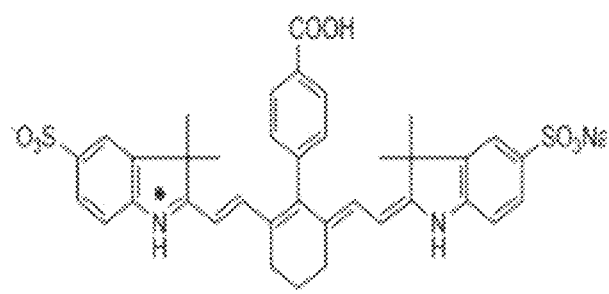
FIG. 1B
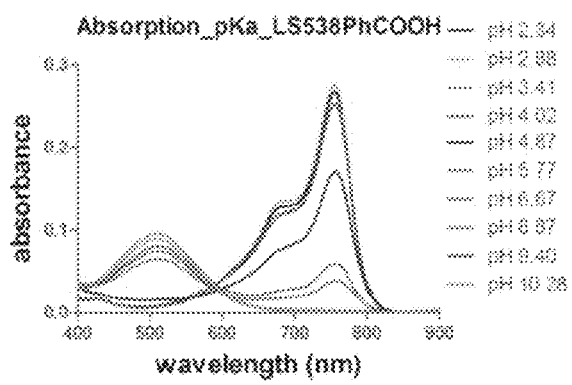
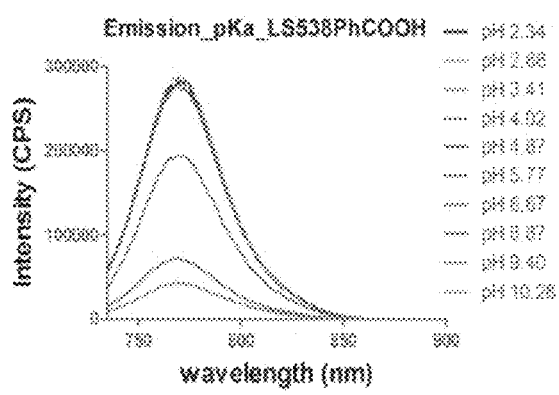
FIG. 1C

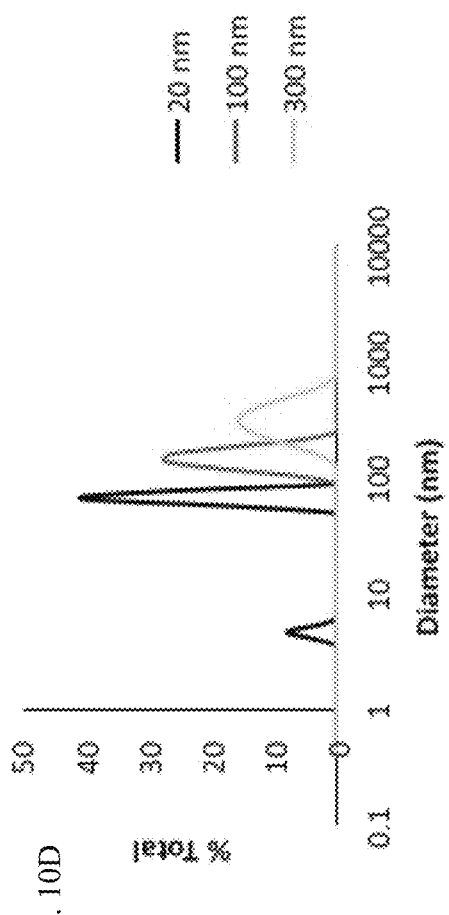
FIG. 10A
FIG. 10B
FIG. 10C
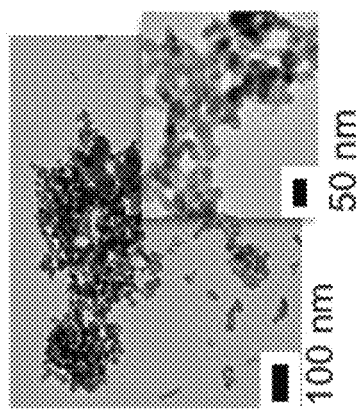
FIG. 10D
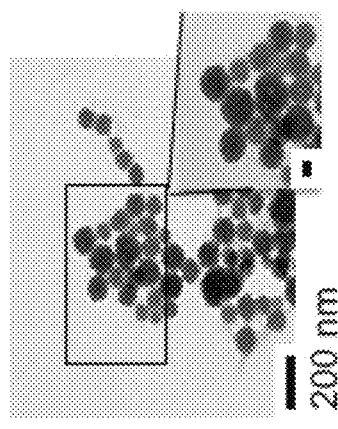
FIG. 10E
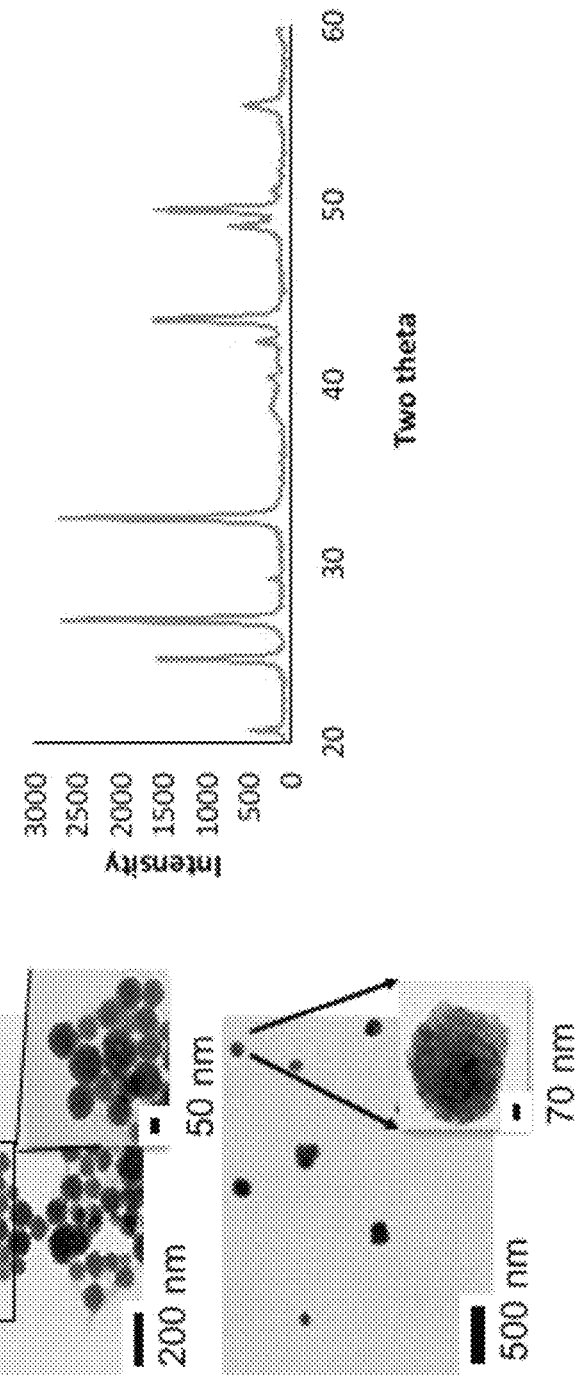

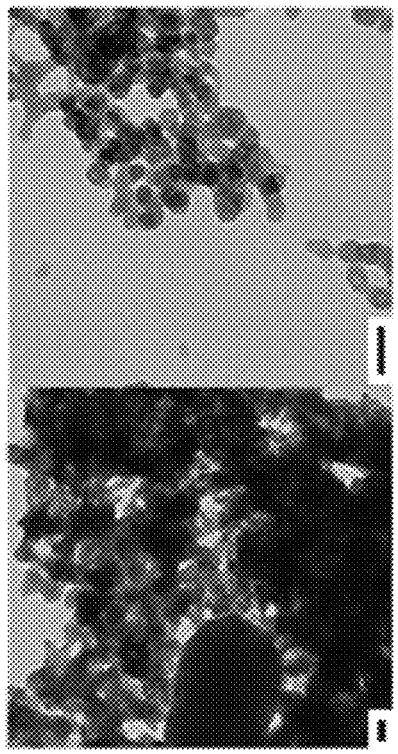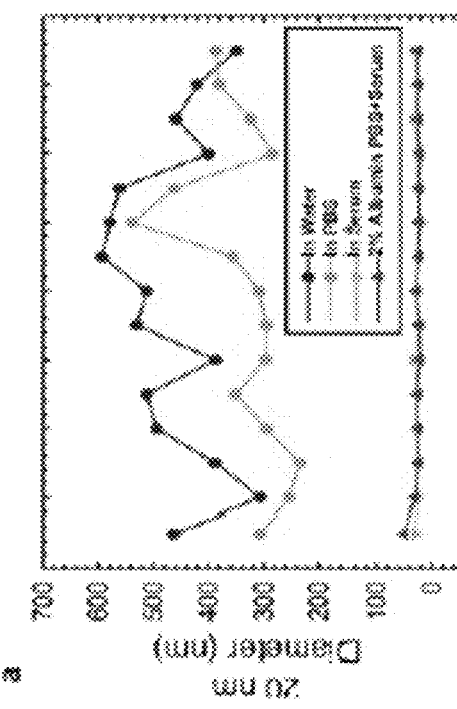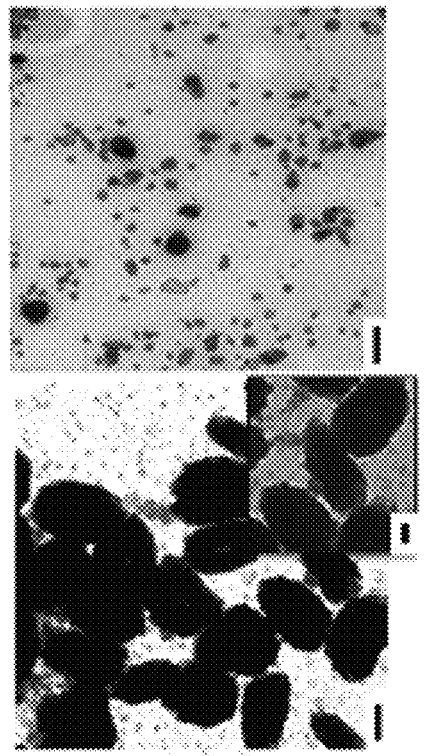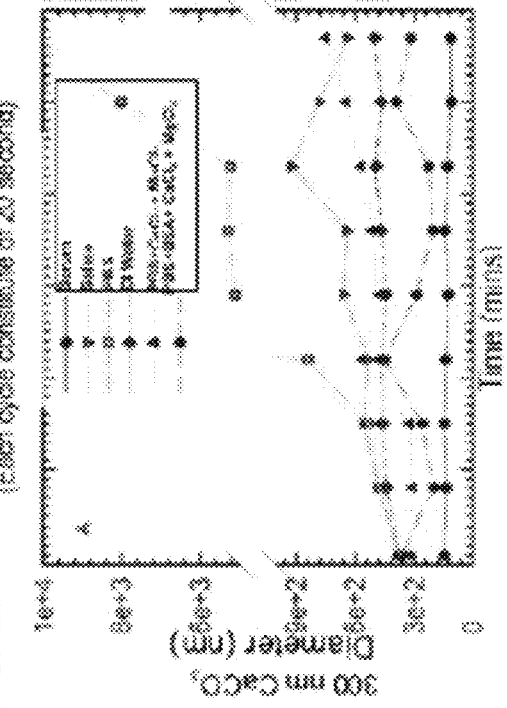
FIG. 12A  FIG. 12B  FIG. 12C
FIG. 12D  FIG. 12E  FIG. 12F

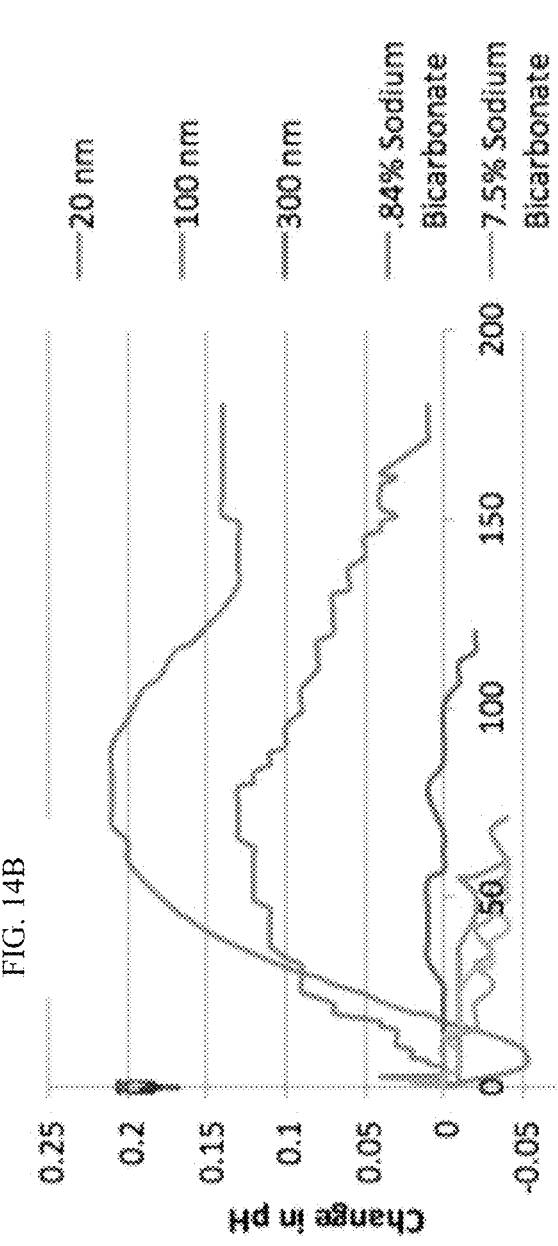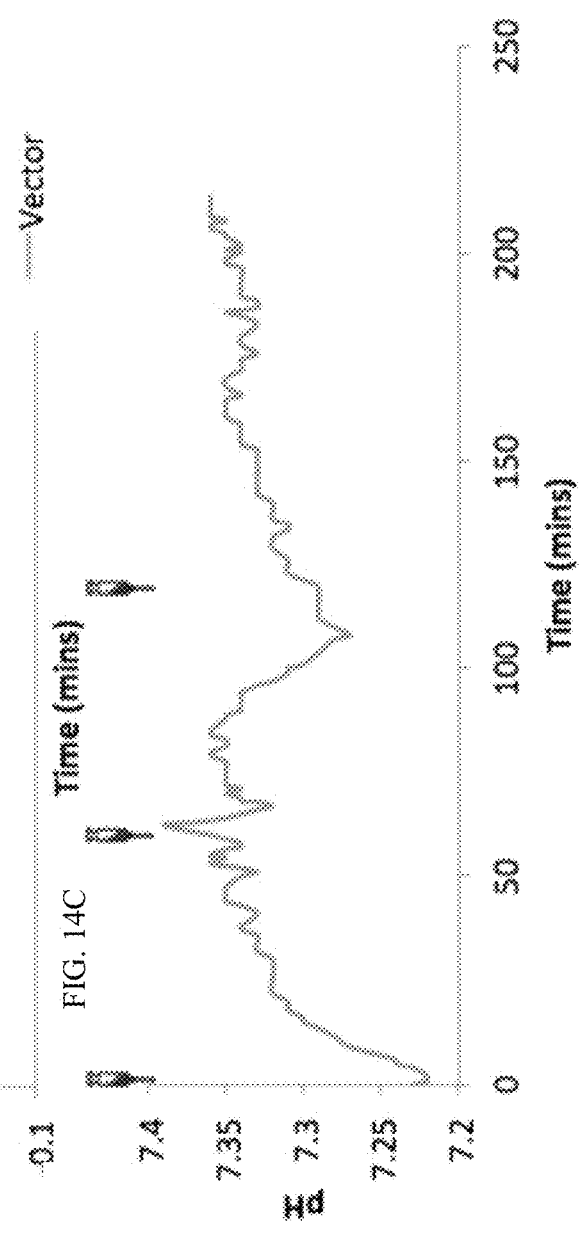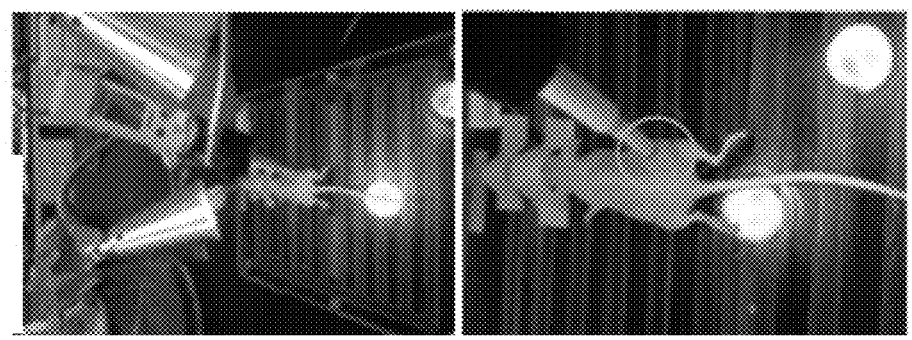

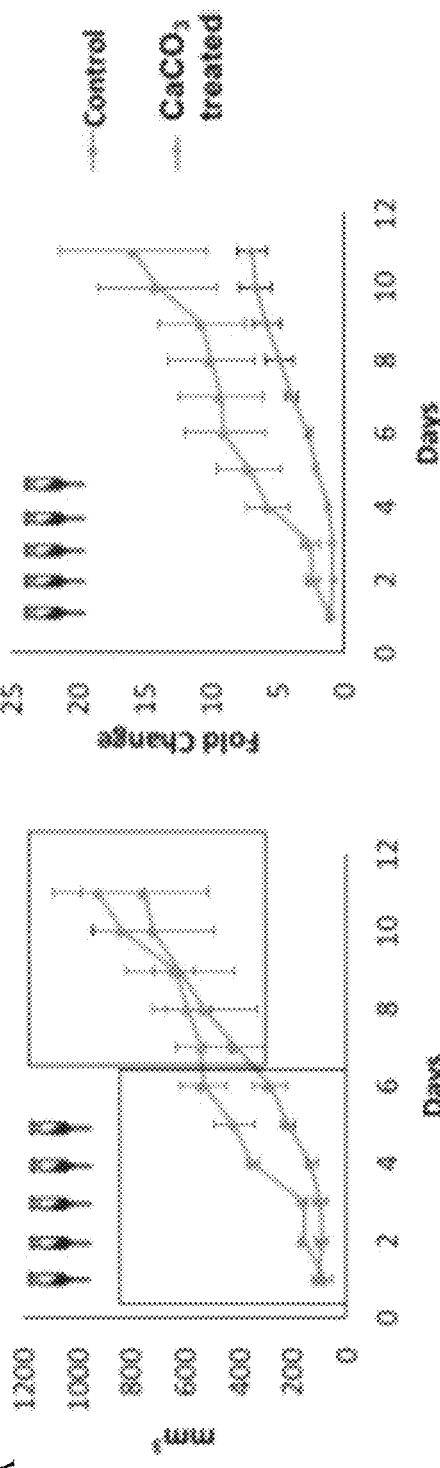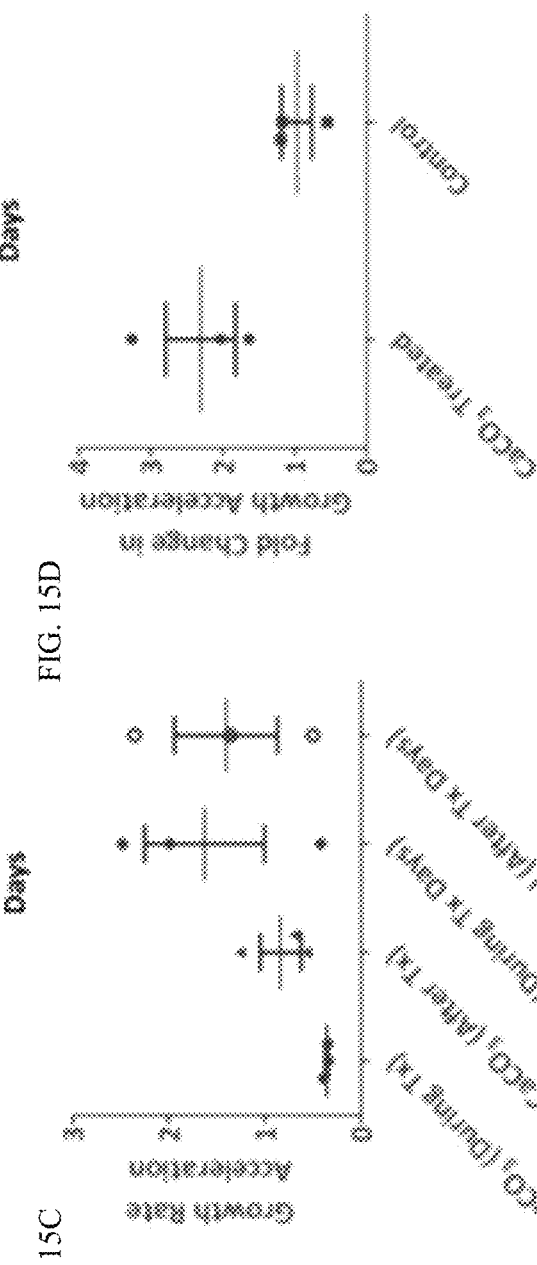
FIG. 15A
FIG. 15B
FIG. 15C
FIG. 15D

NANO-CALCIUM CARBONATE

CROSS-REFERENCE TO RELATED APPLICATIONS

This application claims priority to U.S. Provisional Patent Application Ser. No. 62/257,878, filed on Nov. 20, 2015, which is hereby incorporated by reference in its entirety.

STATEMENT IN SUPPORT FOR FILING A SEQUENCE LISTING

A paper copy of the Sequence Listing and a computer readable form of the Sequence Listing containing the file named "WUSTL015910_ST25.txt", which is 2,051 bytes in size (as measured in MICROSOFT WINDOWS® EXPLORER), are provided herein and are herein incorporated by reference. This Sequence Listing consists of SEQ ID NO:1-4.

BACKGROUND OF THE DISCLOSURE

The present disclosure relates generally to compositions and methods for treating tumors. More particularly, the present disclosure relates to compositions including calcium carbonate nanoparticles and methods for neutralizing extracellular pH by administering the compositions of the present disclosure. Further disclosed are methods for treating cancers by administering the compositions of the present disclosure.

Cancer is now accepted as a disease caused by genomic instability and epigenetic factors. This understanding has ushered in a new set of drugs that target specific molecular pathways used by cancer cells to proliferate and elude the host defense system. Through genomic, proteomic, and metabolomics analyses, several highly successful molecularly targeted therapeutics have been developed such as Dasatinib, which targets tyrosine kinases (CML), and Temsirolimus, which targets mTOR (solid tumors such as renal cell carcinoma). While embodying the paradigm of most current therapeutic research, targeted therapeutics are rarely used for curative intent. Targeted therapeutics are also prone to selecting for resistant subclones, and most importantly, are often effective for only a small subset of clinical patients. Given an average development cost of about 1.8 billion dollars per drug, this inefficiency has clinicians turning towards alternatives, such as screening old drugs for off-label use. In addition, due to the redundancy of intracellular pathways, cells are able to mutate around the targeted pathway, developing resistance. Examples include Imatinib (Anti-BCR-ABL) and anti-Her-2 therapies, whose mechanisms of resistance are now active fields of study. Given the difficulties faced with molecularly targeted chemotherapeutics, these findings support the need to re-explore the hallmarks of cancer as a universal target for cancer therapy.

Malignant tumors rely on several fundamental pathophysiological processes for survival. Targeting these processes is the favored clinical approach because the agents can be widely used to treat diverse cancer types. Thus, most clinical progress involves therapeutics targeted against DNA replication, microtubules, and glycolysis. However, each of these methods has typically severe side-effects, including induced life-threatening immunodeficiency, peripheral neuropathy, and induced cachexia, respectively. Anti-mitotic agents, for example, have deleterious effects on any rapidly dividing normal cells, with life threatening implications from bone marrow loss that can lead to immunodeficiency and life threatening infection. With only a few exceptions, these chemotherapies are rarely curative and alternative compensatory metabolic pathways often lead to drug resistance. For example, glycolysis inhibitors are not effective because this conserved metabolic process is replaced by glutamine consumption from muscles, often leading to cachexia. In addition, any approach that targets intracellular pathways must outwit the upregulation of multidrug resistance (MDR) toxin efflux pumps by tumor cells and their intrinsic ability to mutate/modify these pathways seamlessly.

One unique hallmark of cancer is the acidic extracellular pH ("pHe") found in a diverse range of tumors. Models on tumor pHe demonstrate a relationship between tumor invasiveness and the increased production of acid in most tumors. Increased acidity appears to be correlated to increased tumor invasiveness, with some hypotheses that tumor cells use this four-fold increase in hydrogen ion concentration to degrade the tumor matrix and sustain growth. To maintain normal intracellular pH ("pHi") and to promote growth by degradation of the extracellular matrix, tumor cells actively transport the excess protons generated during enhanced glycolysis, the Warburg effect, to the extratumoral environment. This leads to a sustained acidic tumor environment, with an average extracellular pH of 6.8, as opposed to the buffered and highly regulated interstitial pH of about 7.4 in the vicinity of healthy tissue. Tumor cells actively use this 4 fold increase in hydrogen ion concentration to degrade the tumor matrix and thus sustain its growth.

The vaterite phase of calcium carbonate has biomedical significance due to its versatile properties including high dissolution, dispersivity, and biocompatibility. One of the most prevalent applications of calcium carbonate is as an antacid, which has been studied extensively in past. Calcium carbonate has three common polymorphs; calcite, vaterite and aragonite. Calcite is the most stable while vaterite is the least stable polymorph at room temperature and atmospheric pressure. The thermodynamic instability of the vaterite makes it convert to calcite over time under normal conditions. Due to this instability, the study of antacid properties of nanoscale vaterite phase calcium carbonate has not been completed. Much like other nanomaterials, $CaCO_3$ has unique characteristics in comparison to its bulk counterpart including optical, mechanical, high surface area to volume size ratio, and surface chemical properties. Several attempts have been made to synthesize the meta-stable vaterite form of calcium carbonate, however these particles are either in the size range of a few microns, are not stable for an extended period of time, have low phase purity or require ultra-sonication and heating.

The acidic environment of cancer is a unique condition that can be targeted to treat diverse tumor types. Recently, groups have tried changing the low pH environment of tumors by either inhibiting carbonic anhydrases or directly neutralizing the tumor acid environment via systemic administration of oral sodium bicarbonate. Both of these models have shown efficacy in in vivo animal models. However, carbonic anhydrases are important in normal cell physiology and given the vast class of carbonic anhydrases available to tumors in their genetic material, whether the inhibitors can overcome the system's redundancy, such as that seen in anti-glycolytic drugs, remains unknown. The systemic administration of untargeted oral sodium bicarbonate to directly neutralize the acid environment of tumors is not practicable in clinics because of the potentially severe consequences of metabolic alkalosis. In addition, both of these treatments modify pH only temporarily. Accordingly, there exists a need for therapeutic approaches that primarily modify the extracellular environment and potentially avoid intracellular resistance mechanisms.

SUMMARY OF THE DISCLOSURE

In one aspect, the present disclosure is directed to a composition comprising a calcium carbonate ($CaCO_3$) nanoparticle and albumin.

In another aspect, the present disclosure is directed to a method for neutralizing extracellular pH. The method comprises administering a composition comprising a calcium carbonate ($CaCO_3$) nanoparticle.

In another aspect, the present disclosure is directed to a method for treating cancer in a subject in need thereof. The method comprises administering to a subject in need thereof a composition comprising a calcium carbonate ($CaCO_3$) nanoparticle.

DESCRIPTION OF THE DRAWINGS

The patent or application file contains at least one drawing executed in color. Copies of this patent or patent application publication with color drawing(s) will be provided by the Office upon request and payment of the necessary fee.

The disclosure will be better understood, and features, aspects and advantages other than those set forth above will become apparent when consideration is given to the following detailed description thereof. Such detailed description makes reference to the following drawings, wherein:

FIG. 1A depicts the structure of the pH sensitivity of LS662 dye.

FIGS. 1B and 1C depict LS662 titrated against pH to determine pH sensitivity. Fluorescence appearance around pH 6.67 with a pKa of 4.87 for the compound and fluorescence disappeared by pH 8.87.

FIG. 10A is a TEM of 20 nm vaterite showing rod like particles with a tendency for aggregation.

FIG. 10B is a TEM of 100 nm vaterite showing spherical particles.

FIG. 10C is a TEM of 300 nm vaterite showing larger spherical particles.

FIG. 10D is a graph showing that DLS results in ethanol for the 3 particle sizes replicates TEM findings.

FIG. 10E is a graph depicting XRD of 100 nm $CaCO_3$ demonstrating vaterite signature.

FIG. 12A is a graph depicting DLS results over time in a variety of aqueous solvents for 20 nm particles demonstrates that particles on addition to serum separate from an aggregate in 2% albumin.

FIG. 12B is a TEM of 20 nm particles in PBS+$CaCl_2$+$MgCl_2$+2% albumin shows separation. Scale bar is 200 nm.

FIG. 12C is a TEM of 20 nm particles post serum incubation shows retention of morphology.

FIG. 12D is a graph depicting DLS results over time in a variety of aqueous solvents for 300 nm particles showing the same trend as 20 nm and 100 nm particles in solvent stability.

FIG. 12E is a TEM of 300 nm particles under 2% albumin+PBS showing some slight increase in size. Scale bar for large image is 200 nm. Scale bar for magnified image is 100 nm.

FIG. 12F is a TEM of 300 nm particles in serum showing retention of shape and morphology. Scale bar is 200 nm.

FIG. 14A is an image of the pH measurement setup of I.V. injections of nano-$CaCO_3$. Probe is ~5 mm deep into the tumor, and ~5 mm wide, indicating that any pH value measured was most likely extracellular.

FIG. 14B is a graph depicting the pH change in vivo with 1 mg bolus intravenous injections (time point of injection symbolized on the graph as an injection needle) of $CaCO_3$ particles, bicarbonate, or vector.

FIG. 14C is a graph depicting the pH change with multiple injections of 100 nm particles in HT1080 tumor models demonstrating asymptotic changes near pH of 7.4.

FIG. 15A is a graph depicting repeated administration of 100 nm nano-$CaCO_3$ tumor size during treatment (first box) was significantly lower than control, which partially equalized after treatment ended (second box).

FIG. 15B is a graph depicting the fold change in tumor size was significantly reduced in treated tumors. Controlling for initial size.

FIG. 15C is a graph depicting the decrease in growth rate of treated tumors compared to control during treatments that only partially returned to normal after treatment removal.

FIG. 15D is a graph showing that the removal of $CaCO_3$ doubled the growth rate acceleration of the tumor after treatment removal, with little change in control over the same time period. Error bars represent standard error. Error bars refer to standard error with an n=3 biologic replicates for each arm.

DETAILED DESCRIPTION

Figures 2A, 2B:
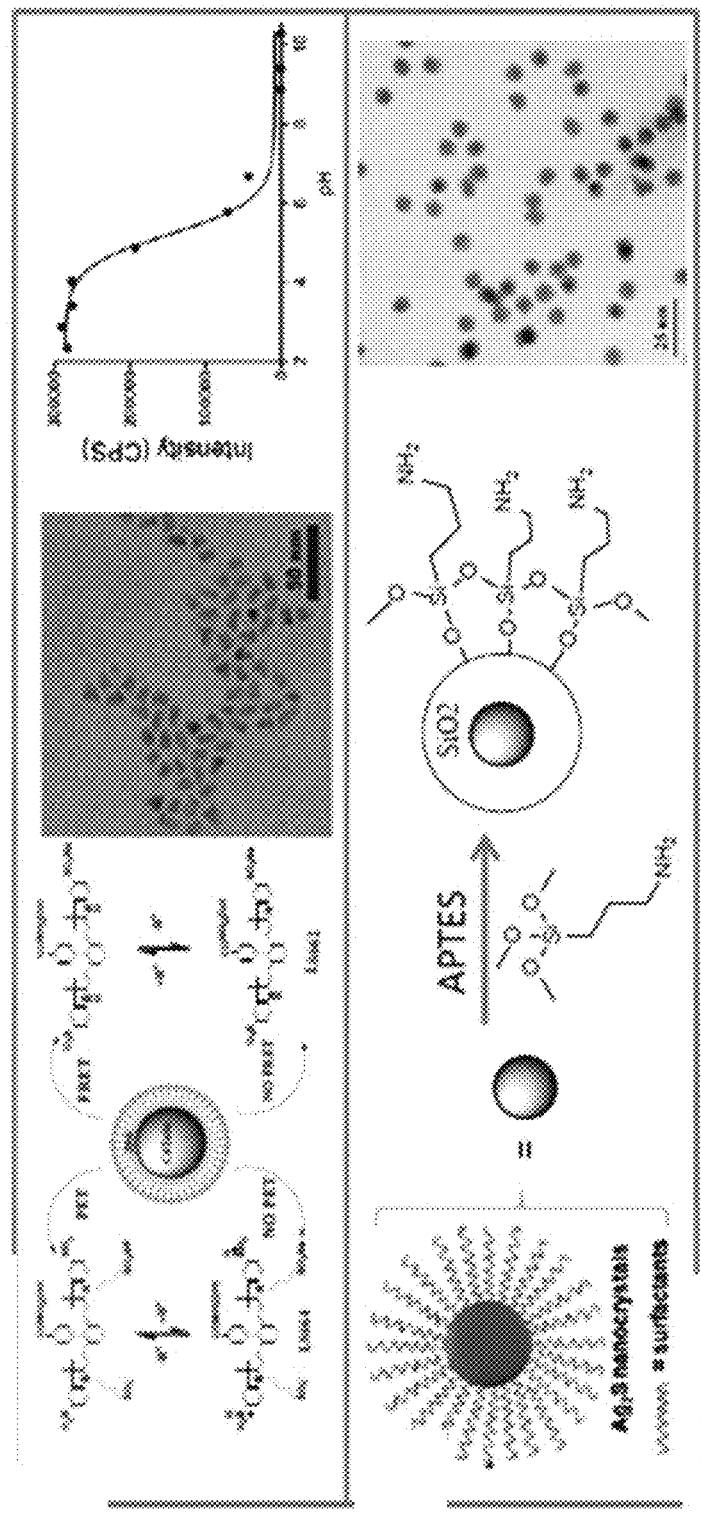
FIG. 2A depicts the synthesis of energy-transfer pH-sensitive quantum dots (left), TEM characterization (middle), and pH-response (right).
FIG. 2B depicts the hydrophobic silver nanoparticles (right) coated with functionalized NIR fluorescence silica (middle), and TEM of the coated nanoparticles (right).

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

As used herein, the methods are directed to be used with a subject in need thereof. More particularly, the methods of the present disclosure are to be used with a subset of subjects who are suspected of having and/or have cancer. Subjects in particular are suspected of having and/or have cancers involving tumors. Subjects may be susceptible to or at elevated risk for cancer due to family history, age, environment, and/or lifestyle. Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for cancer.

Disclosed herein are compositions including calcium carbonate nanoparticles. Also disclosed are methods of reducing extracelluler pH ("pHe") and for treating cancer in a subject in need thereof. Without being bound by theory, it is believed that calcium carbonate nanoparticle-mediated longitudinal and localized extracellular pH neutralization can inhibit tumor growth and provide a synergistic environment for improving traditional intracellular therapies.

In one aspect, the present disclosure is directed to a composition including calcium carbonate nanoparticles (interchangeably referred to herein as "nano-$CaCO_3$" and "nano-$CaCO_3$ particles" and "$CaCO_3$ nanoparticles") and albumin.

In one embodiment, nano-$CaCO_3$ particles can be synthesized using a gas diffusion method. The method includes dissolving $CaCl_2*6H_2O$ in anhydrous ethanol. The resulting solution was transferred to a vessel with a cover containing apertures for gas exchange, such as a beaker covered with PARAFILM having holes punched in the PARAFILM, which is placed in a desiccator surrounded by vials containing excess dry ammonium bicarbonate. The entire system is placed under vacuum. The resultant nano-$CaCO_3$ particles can be centrifuged and dried.

In another embodiment, nano-$CaCO_3$ particles can be synthesized using a sol-gel method. The sol-gel method includes mixing each of $CaCl_2*2H_2O$ and $NaHCO_3$ at room temperature. To prepare ~20 nm nano-$CaCO_3$ particles, the premix solutions of $CaCl_2*2H_2O$ and $NaHCO_3$ is prepared in water and polyethylene glycol (1:5 v/v; average molecular weight 1450 Da). To prepare ~300 nm nano-$CaCO_3$ particles, the premix solutions of $CaCl_2*2H_2O$ and $NaHCO_3$ is prepared in water and ethylene glycol (1:5 v/v; molecular weight 62.07 g/mol). The synthesized $CaCO_3$ particles can be collected by sequentially washing the product with ethanol, methanol and acetone, followed by drying.

Stable vaterite nanoparticles can be synthesized by performing a reaction between calcium chloride dehydrate ($CaCl_2 \cdot 2H_2O$) and sodium bicarbonate ($NaHCO_3$). The rate of growth of the crystals can be controlled by performing the reaction in a mixture of water and ethylene glycol. Suitably, the ratio of water to ethylene glycol is about 1:5. The reaction ensues as shown in equation (1):

$$NaHCO_3(aq) + CaCl_2 \cdot 2H_2O(aq) \rightarrow NaCl(aq) + CO_2(aq) + H_2O \quad (1).$$

The two independent methods to produce pristine submicron vaterite nano-$CaCO_3$ particles with distinct diameter ranging from about 15 nm to about 325 nm. The gas diffusion method of exposing calcium chloride in anhydrous ethanol to ammonium bicarbonate, followed by drying the product, affords a simple and highly reproducible method particularly suitable to prepare nano-$CaCO_3$ particles having a diameter of about 100 nm. The double decomposition reaction method between hydrated calcium chloride and sodium bicarbonate at room temperature provides flexibility in particle size preparation. Size control is achieved by mixing the reactants in A mixture of water/polyethylene glycol at a 1:5 ratio is particularly suitable to prepare nano-$CaCO_3$ particles having a diameter of about 20 nm. A mixture of water/ethylene glycol at a 1:5 ratio is particularly suitable to prepare nano-$CaCO_3$ particles having a diameter of about 300 nm.

The composition also includes albumin. Suitable amounts of albumin ranges from about 0.5% to about 5%, more suitably, about 2%. Without being bound by theory, it is believed that albumin can prevent the rapid conversion of vaterite nanoparticles to calcite or calcium phosphate in aqueous medium and serum. Serum stability conferred on nano-CaCO$_3$ in aqueous albumin solution indicates that this composition is ideal for in vivo applications, where serum is abundant.

In one embodiment, the calcium carbonate nanoparticles can further be coupled to a pH low insertion peptide (pHLIP). Conjugation of pHLIP to a "buffering" calcium carbonate nanoparticle can locally target the calcium carbonate nanoparticle to buffer the extracellular tumor microenvironment and to deliver intracellular cytotoxic drugs and dyes.

pHLIP is an amino acid polypeptide that converts into an alpha helix under physiologically acidic conditions and then inserts itself into the cell's plasma membrane.

A particularly suitable pHLIP includes SEQ ID NO:1 (Ac-ACEQNPIYWARYADWLFTTPLLLLDLALLVDA-DEGTG-COOH). A particularly suitable control non-pH sensitive K-pHLIP amino acid sequence includes SEQ ID NO:2 (Ac-ACEQNPIYWARYAKWLFTTPLLLLKLALL-VDADEGTG-COOH). The cysteine residue (C) in the peptide sequence has been inserted to allow for a selective reaction with maleimide that has been pre-attached to nanoparticles. pHLIP can be synthesized using standard Fmoc chemistry on a Wang Resin and peptides by solid phase peptide synthesis, for example. Peptides can be purified using high pressure liquid chromatography (HPLC), for example. The peptide identity can be confirmed by LC-MS and MALDI (M+4168 Da).

The calcium carbonate nanoparticle of the composition can further include a silica coating. A silica coating advantageously allows for the calcium carbonate nanoparticle to be coupled to the pHLIP. A silica coating also advantageously allows for controlling the calcium carbonate release rate. A standard sol-gel process to coat the CaCO$_3$ with silica and amino functionalized the nanoparticles using (3-Aminopropyl)triethoxysilane (APTES) and ammonia. Functionalized nanoparticles can be characterized by TEM and DLS. Silica coating can be used to increase particle size. The silica coating can further include pores that allow for the controlled release of CaCO$_3$ to neutralize the acidic environment. Suitable pore sizes can be about 2.5 nm The silica coating can be modified in thickness to increase or reduce CaCO$_3$ degradation. The silica coating can be functionalized to be bind to targeting ligand. Both the silica coated and non-silica coated CaCO$_3$ nanoparticles have an ability to neutralize acidic solutions.

The composition can further include hydrophobic alkyl groups on the surface of the silica coated calcium carbonate nanoparticles to minimize interaction of water with the encapsulated CaCO$_3$ nanoparticles.

The calcium carbonate nanoparticle (nano-CaCO$_3$) can further include a therapeutic agent. Suitable therapeutic agents can be, for example, a cytotoxic drug. Suitable cytotoxic drugs include, for example, Doxorubicin, Paclitaxel, among others known to those skilled in the art. In one embodiment, the calcium carbonate nanoparticle is coupled to the amino- (N-) terminus of the pHLIP and the cytotoxic drug is coupled to the carboxy- (C-) terminus of the pHLIP. Thus, the composition of the present disclosure synergistically provides longitudinal and localized extracellular pH neutralization in tumors and intracellular chemotherapy. Additionally, extracellular pH neutralization provided by calcium carbonate released by the composition can constrain the ability of a tumor to grow and invade.

In a particularly suitable embodiment, a calcium carbonate nanoparticle is coupled to the N-terminus of a pHLIP and a cytotoxic drug is coupled to the C-terminus of the pHLIP. In a particularly suitable embodiment, a calcium carbonate nanoparticle is coupled to the N-terminus of a pHLIP and Doxorubicin is coupled to the C-terminus of the pHLIP. In a particularly suitable embodiment, a calcium carbonate nanoparticle comprising a functionalized silica coating is coupled to the N-terminus of a pHLIP and a cytotoxic drug is coupled to the C-terminus of the pHLIP. In a particularly suitable embodiment, a calcium carbonate nanoparticle comprising a functionalized silica coating is coupled to the N-terminus of a pHLIP and Doxorubicin is coupled to the C-terminus of the pHLIP.

To couple the therapeutic agent, a commercially available ε-azido lysine is introduced to the C-terminus of pHLIP to produce Ac-ACEQNPIYWARYADWLFTTPLLLLDLAL-LVDADEGTGK(N$_3$)—COOH (SEQ ID NO:3). A pH-insensitive pHLIP ACEQNPIYWARYAKWLFTTP-LLLLKLALLVDADEGTGK(N$_3$)—COOH (SEQ ID NO:4) can also be produced using the ε-azido lysine technology. The therapeutic agent is combined with the activated bifunctional linker NH$_2$—(CH$_2$)$_2$—S—S—(CH$_2$)$_2$—COOH (where COOH is activated into a cystamine carboxylic acid). Copper-catalyzed click reaction between the azido group of pHLIP and the acetylene group of linker-therapeutic agent will form triazolium pHLIP-therapeutic agent conjugate. Conjugation of the pHLIP-therapeutic agent to the maleimide functionalized silica-coated CaCO$_3$ nanoparticles followed by the addition of a dye will yield a desired nano-CaCO$_3$ pHLIP-therapeutic agent also coupled with a dye. See, FIGS. 6 & 7.

Figure 5:
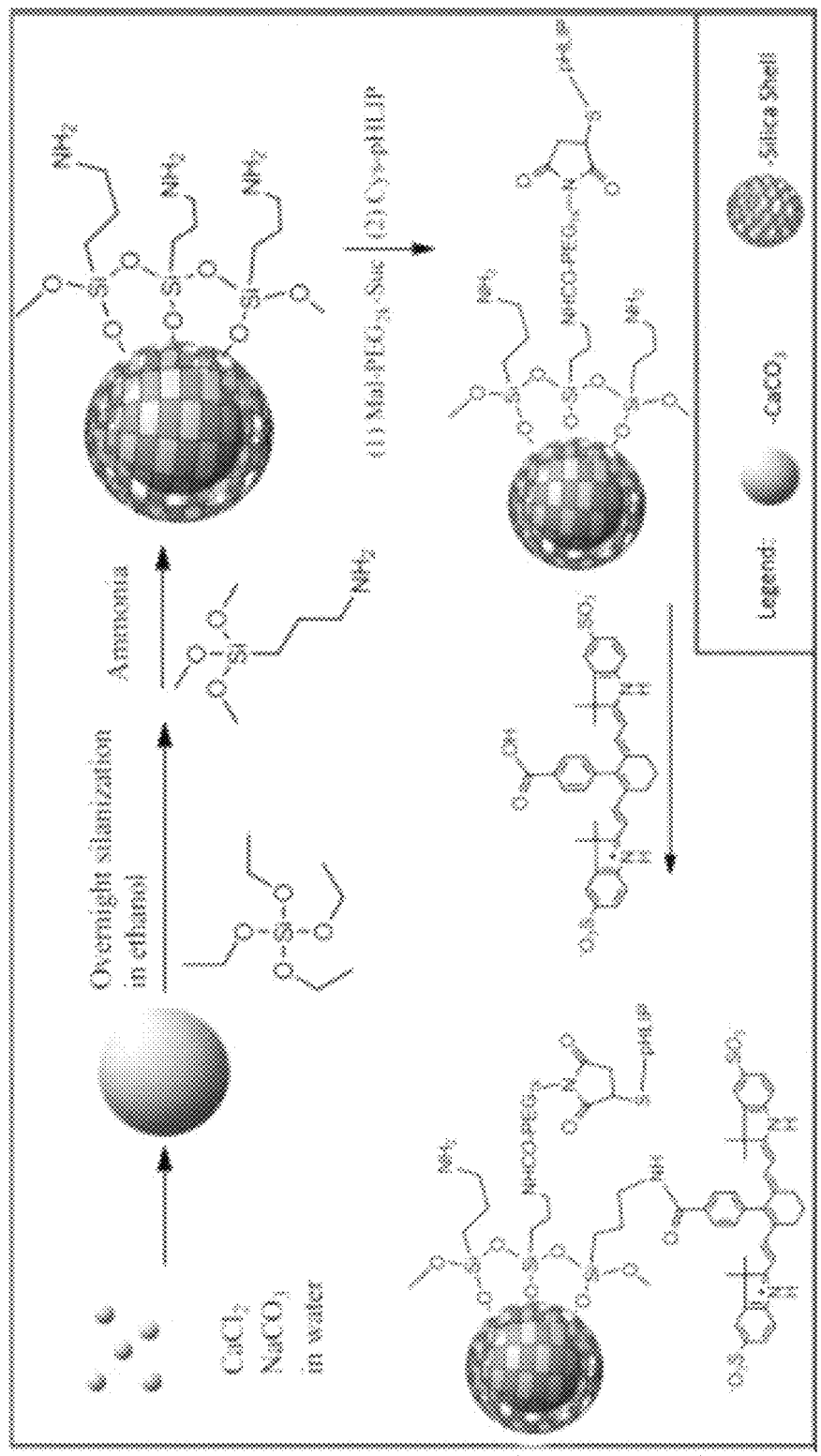
FIG. 5 is a schematic depicting synthesis of a silica coated $CaCO_3$ nanoparticle-pHLIP-dye construct composition of the present disclosure.
Figure 6:
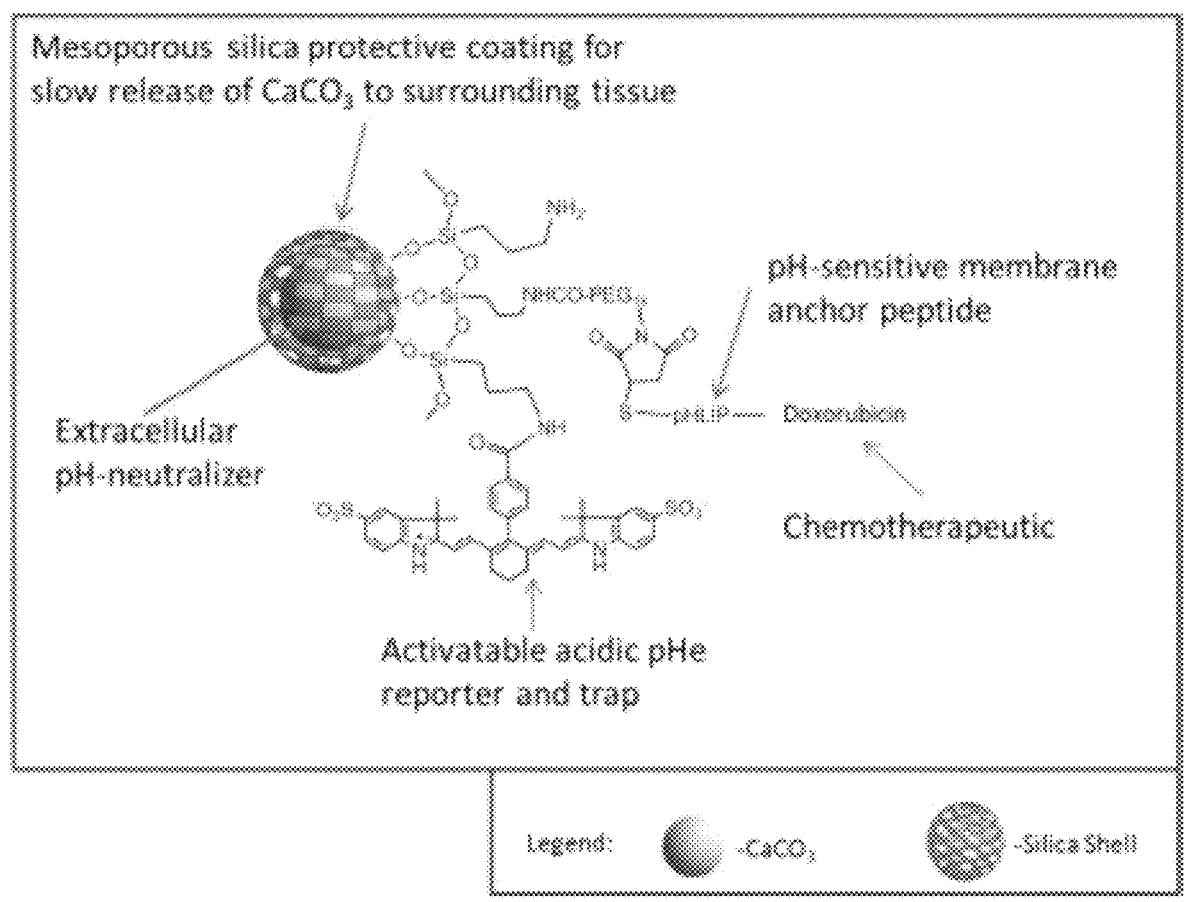
FIG. 6 depicts the structure and functional components of a silica coated $CaCO_3$ nanoparticle-pHLIP-DOX-dye composition of the present disclosure.
Figure 7:
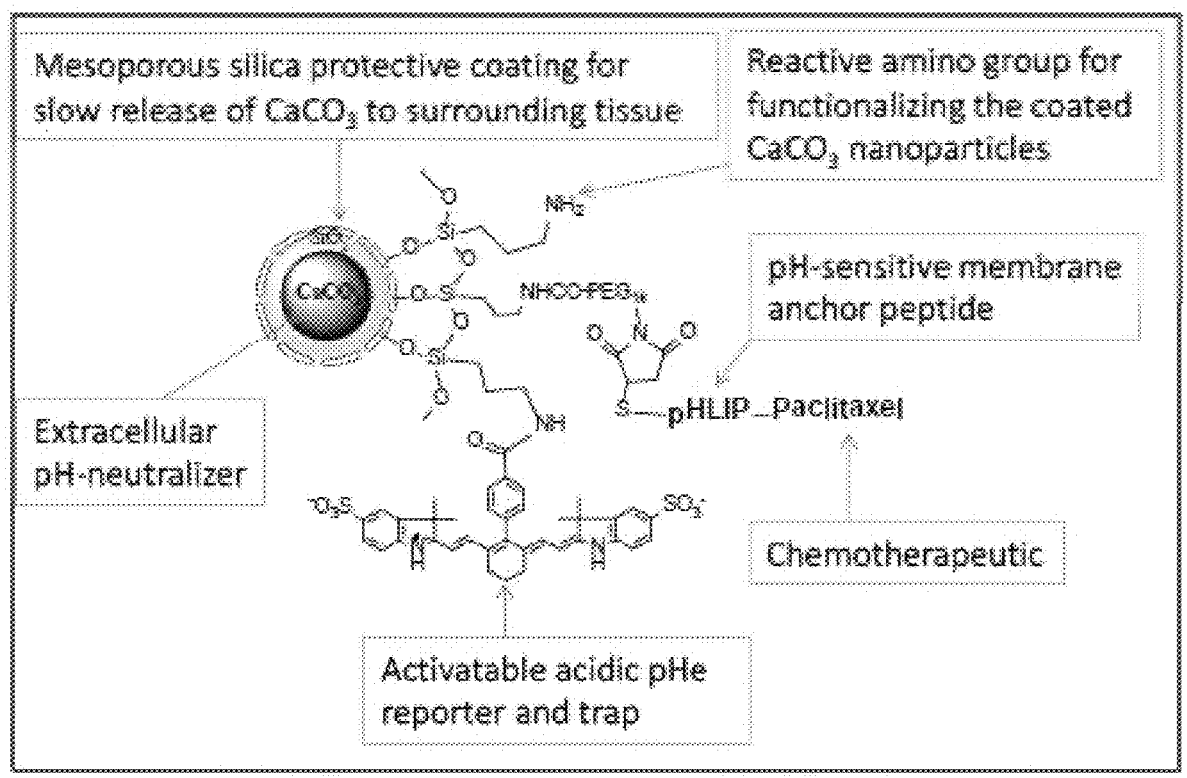
FIG. 7 depicts the structure and functional components of a silica coated $CaCO_3$ nanoparticle-pHLIP-Paclitaxel-dye composition of the present disclosure.

The calcium carbonate nanoparticle can further include a pH-sensitive dye as illustrated in FIGS. 5-7. Including a pH-sensitive dye allows for in vitro and in vivo imaging of nano-pHLIP distribution. A particularly suitable pH-sensitive dye is L662 (illustrated in FIG. 1).

In a particularly suitable embodiment, a calcium carbonate nanoparticle comprising a functionalized silica coating is coupled to the N-terminus of a pHLIP and a pH-sensitive dye is coupled to the unreacted amino groups on the pHLIP-conjugated-nanoparticle. In a particularly suitable embodiment, a calcium carbonate nanoparticle comprising a functionalized silica coating is coupled to the N-terminus of a pHLIP and LS662 is coupled to the unreacted amino groups on the pHLIP-conjugated-nanoparticle via succinimidyl ester of the pH-sensitive dye.

In another embodiment, a calcium carbonate nanoparticle is coupled to the N-terminus of a pHLIP and a dye is coupled to the C-terminus of the pHLIP. In a particularly suitable embodiment, a calcium carbonate nanoparticle is coupled to the N-terminus of a pHLIP and a pH-sensitive dye is coupled to the C-terminus of the pHLIP. In a particularly suitable embodiment, a calcium carbonate nanoparticle comprising a functionalized silica coating is coupled to the N-terminus of a pHLIP and a pH-sensitive dye is coupled to the C-terminus of the pHLIP. In a particularly suitable embodiment, a calcium carbonate nanoparticle comprising a functionalized silica coating is coupled to the N-terminus of a pHLIP and LS662 is coupled to the C-terminus of the pHLIP.

Calcium carbonate nanoparticles can be synthesized according to the methods disclosed herein. Nano-CaCO$_3$ particles can be synthesized in a variety of sizes ranging from about 20 nm to about 500 nm. Nano-CaCO$_3$ particles size can be measured by methods known to those skilled in the art. For example, calcium carbonate nanoparticle size can be determined by measuring nanoparticle images from transmission electron micrographs.

Calcium carbonate nanoparticles can be siliconized as illustrated in FIGS. 5-7. The pHLIP can be coupled (or conjugated to) siliconized calcium carbonate nanoparticles by methods known to those skilled in the art and as illustrated in FIGS. 5-7. The therapeutic agent and dye can be conjugated to the pHLIP by methods known to those skilled in the art and as illustrated in FIGS. 5-7.

Suitable linkers can be used to separate the nano-CaCO₃ particles from the pHLIP. Without being bound by theory, separation of the calcium carbonate nanoparticle and the pHLIP can minimize any possible interference from both premature pH neutralization and the conformational changes required for pHLIP internalization. To allow intracellular delivery of a therapeutic agent, a disulfide cleavable linker that can be used. The disulfide cleavable linker can be reduced in the intracellular environment, thereby allowing the agent's therapeutic effect to occur in the cell. Another suitable linker can be an ester linkage, which is more slowly hydrolyzed than the disulfide linker.

In another aspect, the present disclosure is directed to a method for neutralizing extracellular pH. The method includes administering a composition comprising a calcium carbonate ($CaCO_3$) nanoparticle. In one embodiment, the composition further includes albumin. Suitable amounts of albumin range from about 0.5% to about 5%, more suitably, about 2%.

The calcium carbonate ($CaCO_3$) nanoparticle can further be coupled to a pHLIP as described herein. The calcium carbonate ($CaCO_3$) nanoparticle can further include a silica coating as described herein. A silica coating advantageously allows for the calcium carbonate nanoparticle to be coupled to the pHLIP. A silica coating also advantageously allows for controlling the calcium carbonate release rate. The silica coating also allows for the controlled release of $CaCO_3$ to neutralize the acidic environment. The coating can be modified in thickness to increase or reduce $CaCO_3$ degradation.

The composition can further include hydrophobic alkyl groups on the surface of the silica coated calcium carbonate nanoparticles to minimize interaction of water with the encapsulated $CaCO_3$ nanoparticles.

The composition can further include a therapeutic agent as described herein.

The composition can further include a pH-sensitive dye as described herein.

In another aspect, the present disclosure is directed to a method for treating cancer in a subject in need thereof. The method comprises administering to a subject in need thereof a composition comprising a calcium carbonate ($CaCO_3$) nanoparticle.

The calcium carbonate ($CaCO_3$) nanoparticle can further include a silica coating as described herein. A silica coating advantageously allows for the calcium carbonate nanoparticle to be coupled to a pHLIP. A silica coating also advantageously allows for controlling the calcium carbonate release rate. The silica coating also allows for the controlled release of $CaCO_3$ to neutralize the acidic environment. The coating can be modified in thickness to increase or reduce $CaCO_3$ degradation.

The composition can further include hydrophobic alkyl groups on the surface of the silica coated calcium carbonate nanoparticles to minimize interaction of water with the encapsulated $CaCO_3$ nanoparticles.

The composition can further include a therapeutic agent as described herein.

The composition can further include a pH-sensitive dye as described herein.

The disclosure will be more fully understood upon consideration of the following non-limiting Examples.

EXAMPLES

Example 1

In this Example, the synthesis of a pH sensitive dye, its conjugation to $CaCO_3$ nanoparticles, its tumor targeting and delivery of DOX to tumors using the $CaCO_3$ nanoparticles was investigated.

Synthesis of pH sensitive dye for monitoring treatment targeting and efficacy. The structure of the pH-sensitive dye LS662 is shown in FIG. 1. At neutral pH, LS662 was practically not fluorescent, but upon protonation of the secondary amines around pH 6.7, NIR fluorescence was emitted, demonstrating the pH sensitivity of this dye for imaging the acidic extracellular matrix of tumors (FIGS. 1B and 1C).

pH-sensitive dyes were conjugated to quantum dots (FIG. 2A). The pH-properties of the small organic dye transferred to the quantum dots' luminescence as analyzed through fluorescence resonance energy transfer. Hydrophobic silver quantum dots were also prepared and coated with silica, which added about 2 nm to the particles size and transformed the hydrophobic nanoparticles to water-soluble nanoparticles (FIG. 2B). These data illustrate the ability to prepare the silica-coated $CaCO_3$ materials.

Figure 3:
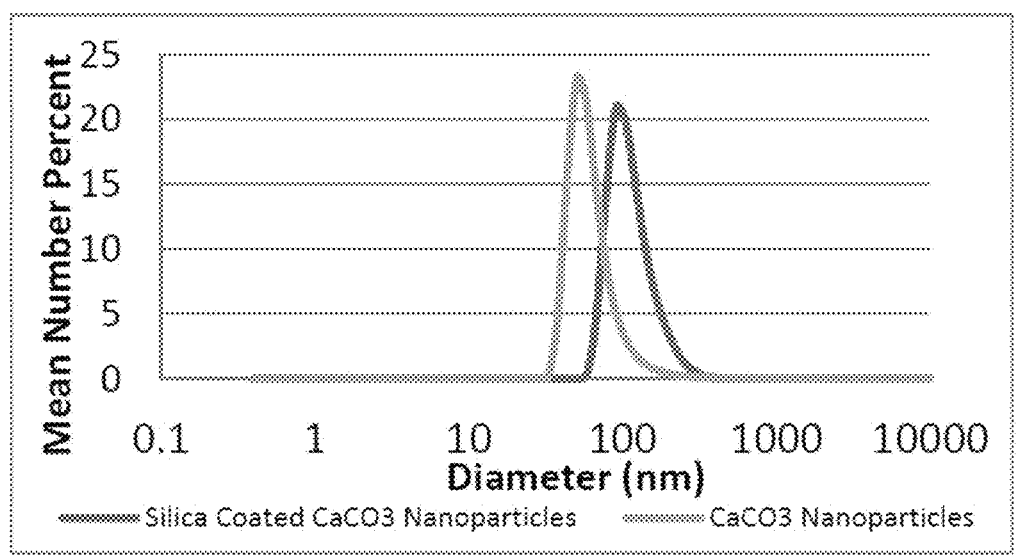
FIG. 3 depicts the size distribution of $CaCO_3$ nanoparticles and silica coated $CaCO_3$ nanoparticle. The size distribution increases following salinization as measured by DLS and zeta potential.

A silica coated $CaCO_3$ nanoparticle was developed that was amino functionalized to be bound to targeting ligand. As illustrated in FIG. 3, DLS and zeta potential results showed an increase in $CaCO_3$ nanoparticle following silica coating. Silica coating causes an increase of about 40 nm in particle size (peak centered at 100 nm). Silica coating in addition caused a Zeta potential change of 10 mV ($CaCO_3$: −25.1 mV, Silica Coated: −14.9).

Figure 4B:
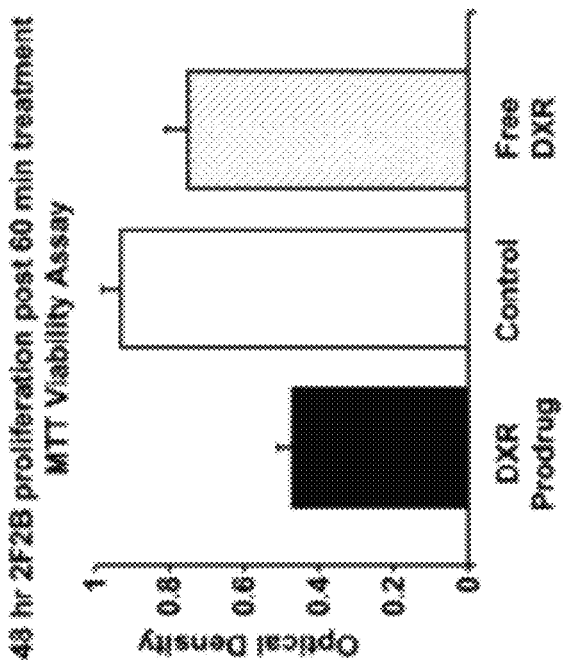
FIG. 4B is a graph depicting the effectiveness of DOX nanoparticles was greater (p<0.05) than free drug over 48 h proliferation study post 60 min treatment using MTT Viability assay.
Figure 4A:
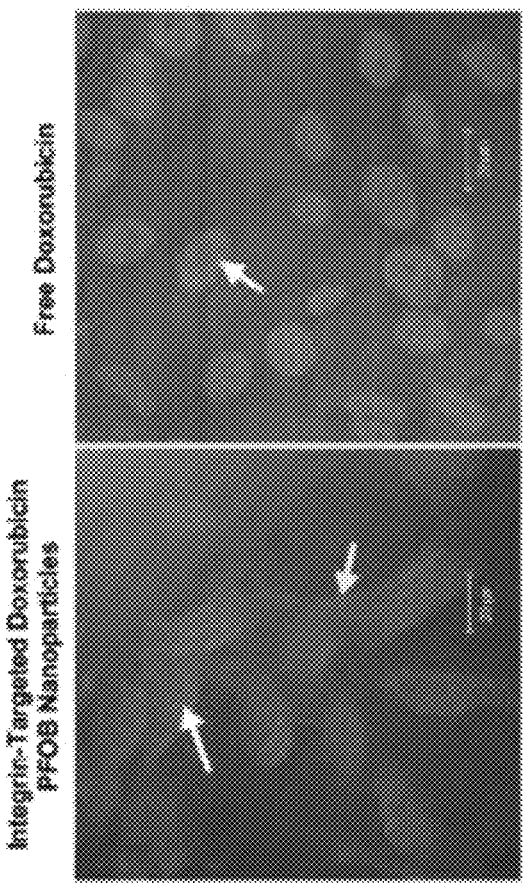
FIG. 4A depicts fluorescent micrographs showing 2F2B cells treated for 30 min with αvβ3-targeted perfluorocarbon nanoparticles incorporating DOX (Left) vs. equimolar exposure of free DOX (Middle).

Encapsulation of DOX in perfluorocarbon nanoparticles released a large amount of the drug in the tumor cells relative to control or free DOX (FIG. 4). Not only was significant amount delivered to the nucleus (white arrow), the cytoplasmic content of DOX remained high (yellow arrow), providing a continuous source of DOX for nuclear translocation. In contrast, the cytoplasmic content of the free DOX-treated cells were depleted rapidly. With about 50% survival, this result demonstrates the challenges of intracellular cell killing mechanism alone, which we expect to overcome with the dual proposed dual-mode therapy. The data also confirm that DOX fluorescence, which was used to obtain these images, will provide sufficient contrast for imaging DOX's intracellular trafficking to the nuclei.

Synthesis of pHLIP: Synthesis of short and long peptides was facilitated by a microwave peptide synthesizer equipped with a UV monitoring system that automatically adjusts the deprotection or coupling modules of the synthesis to improve product yield. We used the synthesizer to prepare the 37 amino acid sequence of pHLIP, consisting of: ACEQNPI-YWARYA-DWLFTTPLLLLDLALLVDADE-GTG. The pHLIP was synthesized using standard Fmoc chemistry on a Wang Resin. The peptide was precipitated with cold MTBE and lyophilized. The peptide identity was confirmed by MALDI (M+4168 Da). The pHLIP was coupled with the $CaCO_3$ nanoparticles as described above.

The structure and functional components of a silica $CaCO_3$ nanoparticle-pHLIP-LS662 composition is illustrated in FIG. 5. The structure and functional components of a silica $CaCO_3$ nanoparticle-pHLIP-DOX-LS662 is shown in FIG. 6. The structure and functional components of a silica $CaCO_3$ nanoparticle-pHLIP-Paclitaxel-LS662 is shown in FIG. 7.

Figure 8A:
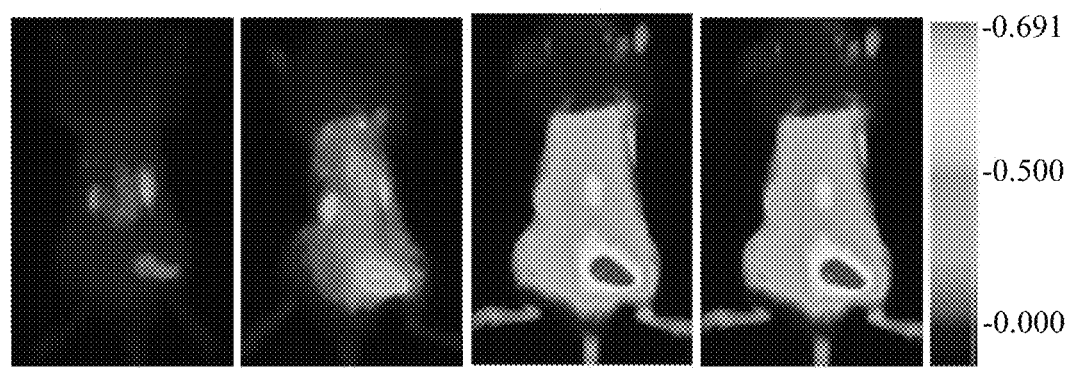
FIG. 8A depicts in vivo imaging of the distribution of a peptide-labeled LS662 in 4T1luc murine model (blue—low; red—high fluorescence).
Figure 8B:
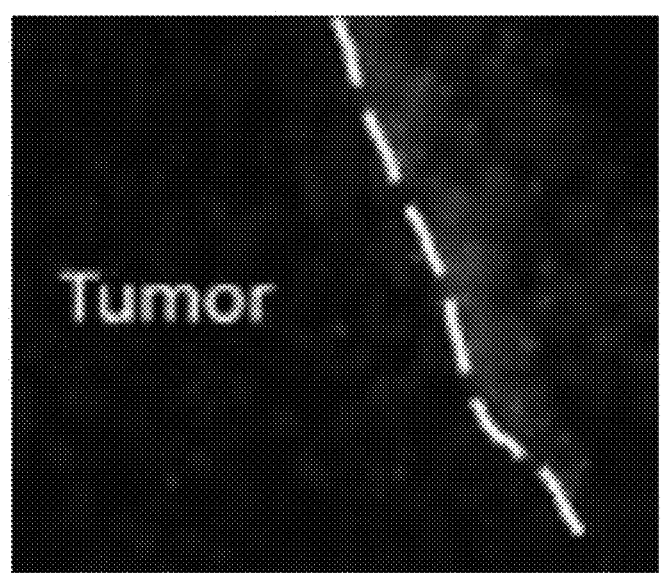
FIG. 8B depicts peptide-labeled LS662 retention in the acidic intratumoral space.

To mimic the proposed conjugation of LS662 to $CaCO_3$ nanoparticle-pHLIP, a peptide-LS662 conjugate was prepared and evaluated its ability to localize in the acidic environment of 4T1luc tumor following protonation of the amino group. There was low fluorescence at physiological pH, as expected, but the acidic environment of tumors was detectable within 30 min post injection. The increased readily, attaining a maximum at 24 h, and remained at this level until the mice were euthanized 4 days later (FIG. 8A). Ex vivo analysis showed that the NIR (red) fluorescence was primarily in the extra-tumoral tissue (FIG. 8A). The dotted vertical line shows the tumor margin (FIG. 8B), which was validated by histologic analysis (data not shown). This result demonstrates that LS662 can assist in trapping $CaCO_3$ nanoparticle-pHLIP-LS662 in the extracellular matrix of tumors, ensuring adequate time for pHLIP protonation and the eventual anchoring in tumor cells.

Example 2

In this Example, methods to prepare monodispersed $CaCO_3$ nanoparticles of particular size and stability are described.

In the solid state, $CaCO_3$ exists predominantly as calcite, aragonite, or vaterite polymorphs. These polymorphs differ in their crystal lattice structures. Because $CaCO_3$ dissolution is regulated by basic rate equations, a simulation of its dissolution and prediction of the expected pH changes in vivo and in vitro is possible. Simulations were run in MATLAB using a numerical iteration approximation. Equations (1-6) are derived from a tissue cylinder model of diffusion and diffusion of $CaCO_3$ from a nanoparticle under the conditions of constant infusion. Equations (5) and (6) were used to determine the initial $CaCO_3$ and pH distributions in the tissue cylinder model. Changes in $CaCO_3$ and pH were then numerically approximated using equations (3) and (4).

$$\text{(s)} \rightleftharpoons Ca^{2+} + CO_3^{2-} \quad (K_{a1} = 4.45 \times 10^{-7}) \tag{1a}$$

$$H_2O + HCO_3^- \rightleftharpoons H_3O^+ + CO_3^{2-} \quad (K_{a2} = 4.69 \times 10^{-11}) \tag{1b}$$

$$H_2O + H_2CO_3 \rightleftharpoons H_3O^+ + HCO_3^- \tag{1c}$$

$$\text{Solubility } C_b = \sqrt{\frac{K_{sp}}{\frac{K_{a1} * K_{a2}}{((10^{-pH})^2 + K_{a1}10^{-pH} + K_{a1}K_{a2})}}} \tag{2}$$

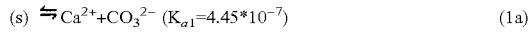

$$J = -D\frac{dC}{dx} \rightarrow \frac{\partial C}{\partial t} = \tag{3}$$

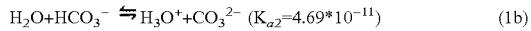

$$\frac{A}{V}D\frac{(C_s - C_b)}{d} \rightarrow \frac{\partial m}{\partial t} = AD\frac{(C_s - C_b)}{d} \rightarrow \frac{\partial r_p}{\partial t} = \frac{D}{\rho}\frac{(C_s - C_b)}{d}$$

$$\frac{dpH}{dt} = -\frac{D}{B}\frac{(C_s - C_b)}{d} * \frac{1}{L} \tag{4}$$

$$[CaCO_3] = \frac{R_{cmax}}{4D_c}(r_c^2 - r^2) + \frac{R_{cmax}r_c^2}{2D_c}\ln\left|\frac{r}{r_c}\right| + k * C_d \tag{5}$$

$$[H^+] = \frac{R_{pmax}}{4D_p}(r^2 - r_c^2) + \frac{R_{pmax}r_c^2}{2D_p}\ln\left|\frac{r_c}{r}\right| + 10^{-7.4} \tag{6}$$

Solubility of $CaCO_3$ ($C_b$), in equation (2) is a function of pH, the solubility product ($K_{sp}$), and equilibrium constants $K_{a1}$ and $K_{a2}$, obtained from equations (1a, 1b). The rate of change in $CaCO_3$ concentration (C) and in particle radius (r), seen in equation (3), are derived from Fick's law, and is a function of the diffusion coefficient (D), the surface area of diffusion (A), the distance of diffusion (d) estimated at 0.1 mm, the solubility of $CaCO_3$ ($C_b$), the volume of the tissue cylinder (C), and the concentration of $CaCO_3$ in vivo ($C_s$). For equation (4), we simplified equation (3) by approximating A/V to 1/L, where L is the length of the tissue cylinder, estimated at 1 mm. The change in concentration of protons can then be converted to a change in a pH of a buffer by dividing by buffering constant, B=28 mM/pH.

For equation (5), $R_{cmax}$ was empirically determined by starting at the maximum degradation rate in the tissue at pH of 6.65 and then multiplying by a correction factor until the distribution of $CaCO_3$ appeared optimal, in this case approximately 0.5 mm from the capillary. The resulting degradation correction factor was used throughout for simulating $CaCO_3$ degradation. The radius of the capillary ($r_c$) was set at 10 μm. The partition coefficient (k) of the capillary is dependent on the capillary pore radius, estimated at 500 nm and particle radius, defined as 100 nm. The initial concentration of $CaCO_3$ ($C_d$) in the capillary was estimated as 5% of the infused concentration (set as 1 mg in a 20 g mouse).

100 nm $CaCO_3$ nanoparticles were synthesized using a gas diffusion method. $CaCl_2 \cdot 6H_2O$ (220 mg) was dissolved by vortexing in anhydrous ethanol (50 mL). The resulting solution was transferred to a 100 mL beaker covered with parafilm. After puncturing small holes in the parafilm, the beaker was placed in a desiccator (with drierite) surrounded by four 20 mL vials containing excess dry ammonium bicarbonate (~9-10 g). The entire system was placed under vacuum for 25 hours. The particles were centrifuged at 6800 g for 10 min, excess ethanol decanted, and the residue was left to dry in open air before use.

A double decomposition reaction was used to prepare 20 and 300 nm $CaCO_3$ particles by mixing 0.1 M each of $CaCl_2 \cdot 2H_2O$ and $NaHCO_3$ at room temperature. The premix solutions of $CaCl_2 \cdot 2H_2O$ and $NaHCO_3$ were prepared in water and polyethylene glycol (1:5 v/v; average molecular weight 1450 Da) for ~20 nm, and water and ethylene glycol (1:5 v/v; molecular weight 62.07 g/mol) for ~300 nm particles. The synthesized $CaCO_3$ particles were collected by sequentially washing the product with ethanol, methanol and acetone, followed by drying at 60° C. for 1 hour.

Transmission electron microscopy (TEM) micrographs were obtained using a FBI Spirit TEM (Hillsboro, USA) operated at 120 kV. A 400-mesh FORMVAR® carbon-coated copper grid was glow-discharged in a vacuum evaporator (Denton, Moorestown, N.J.) for 30 seconds. The sample was prepared by placing 2 μL of sonicated $CaCO_3$ nanoparticles solution onto the grid and wicking off the excess sample with filter paper after 30 seconds. Alternatively, for EtOH or DMSO solvent based solutions, 3 μL of particle solution were placed on the grid and left to dry out at room temperature or with the aid of a heat gun.

X-Ray Diffraction (XRD) patterns were obtained by using the Bruker d8 Advance X-ray Diffractometer (Bruker, USA) configured with a Cu X-Ray tube with 1.5418 Å for analysis of powder samples using LYNXEYE_XE detector. For the analysis, fine acetone ground $CaCO_3$ nanoparticles were kept on a Zero Diffraction Plate (MTI Corporation, USA). XRD data were scanned from 20-60 degrees, with a 0.04 degree step size, a 0.5 s per step count time, with sample rotation turned on (15 rotations per mM), with a coupled two-theta/theta scan. The Bruker Diffrac.Eva program was used for the evaluation and processing of X-ray diffraction scan data. Search-match operations included search by DI list, by name, using chemistry filters, and creating an International Centre for Diffraction Data (ICCDD PDF) database filter.

To study agglomeration kinetics of $CaCO_3$ nanoparticles, hydrodynamic diameter (Dh) was measured using DLS (Malvern Instruments, Southborough, Mass.). Agglomeration kinetics were measured on the basis of data obtained from TR-DLS. The zeta potential was measured using a Malvern Zetasizer Nano ZS instrument. An applied voltage of 100 V was used for the nanoparticles. A minimum of three measurements were made per sample.

For identifying stable aqueous medium for nano-$CaCO_3$, Nano-$CaCO_3$ was resuspended in the following solvents: (1) $dIH_2O$; (2) Dulbecco's PBS, (3) PBS, 1 mM $CaCl_2$, and 1 mM $MgCl_2$; (4) PBS, $CaCl_2$, $MgCl_2$ and 2% bovine serum albumin; (5) fetal bovine serum (FBS); and (6) a solution of 20% PBS, $CaCl_2$, $MgCl_2$, and 2% bovine serum albumin in 80% FBS. The results of particle stability were analyzed by TR-DLS for up to 7 hours, TEM under aqueous conditions, TEM under serum, and XRD after 7 hours.

To determine pH change in acidic media versus normal media $CaCO_3$ dissolution over time pH changes were measured in conditioned acidic media and fetal bovine serum. Conditioned media was from a 7 day incubation of media with HT1080 cells and an initial pH ~6.2. Final concentrations of $CaCO_3$ in the cell free solutions were controlled at 0.67 mg/mL. $CaCO_3$ was added to conditioned media or serum in μ10 μL of aqueous vector (PBS+$CaCl_2$+$MgCl_2$+ 2% bovine serum albumin) under hypoxic 5% $CO_2$ conditions. The pH was then measured after 1 hour.

To determine nano-$CaCO_3$ dose-dependent pH changes in HT1080 cell culture medium, HT1080 cells were plated at 105 cells/well in a 24 well plate overnight under hypoxic conditions (0.3% $O_2$ and 5% $CO_2$), and then incubated with increasing amounts of 20 nm, 100 nm and 300 nm particles for 24 and 96 h. The particles were directly added and resuspended in media via vortexing under hypoxic conditions (0.3% $O_2$ and 5% $CO_2$). The pH was measured after 24 and 96 h incubation. n=3 for each sample.

All animal studies were conducted in accordance with protocols approved by the Washington University Animal Studies Committee. Mice were purchased from Charles River Laboratory.

For determining pHe changes in vivo post bolus particle Intravenous injection, HT1080 tumors were grown subcutaneously in dorsal flanks of athymic nude mice, in dorsal bilateral flanks. Tumors generally grew in one flank. When the tumors growth reached approximately 50 $mm^3$ or greater, the extracellular pH was measured using an external pH electrode. Prior to these experiments, the mice had daily I.V. $CaCO_3$ (1 mg) treatments for 3 weeks. Treatments were discontinued for at least 5 days before performing the in vivo pH measurements. The average initial pH was 6.94+/−0.147. The pH was measured using an extracellular pH electrode implanted into the tumor following a 15 min equilibration period after electrode entry. The pH electrode was calibrated within the week. About 1 mg of each size of particles (20 nm, 100 nm, 300 nm) in a 100 μL solution of PBS, $CaCl_2$, $MgCl_2$ and 2% bovine serum albumin was injected intravenously in individual mice. Approximately 100 μL of aqueous vector (PBS, $CaCl_2$, $MgCl_2$, and 2% bovine serum albumin), 100 μL of 0.84% sodium bicarbonate in deionized (dI) water, and 100 μL of 7.5% sodium bicarbonate in dI water were each serially injected intravenously into the same mouse with 1 hour gaps for measurement. Tumor sizes at time of injection for this experiment were 12 mm×9 mm (20 nm particles), 13.7 mm×12.5 mm (100 nm), 13.5 mm×15.5 mm (300 nm), 12.5×16.5 mm (0.84% bicarbonate), 12.5×16.5 mm (7.5% bicarbonate), and 12.5×16.5 mm (vector). In general, the pH was then followed each minute for a minimum of 1 hour, or up to 3 hours if any changes were seen. Animals tolerated the pH measurement procedure for approximately 4 hours and exhibited complete recovery after treatment. Bleeding, if any, was also noted.

For measuring pH increases post multiple injections, HT1080 tumors were grown subcutaneously in the dorsal bilateral flanks of athymic nude mice. Typically, tumors grew in one flank. When grown to approximately 8.5 mm×8.5 mm, extracellular pH was measured using an external pH electrode. The pH was measured initially following a 15 minutes equilibration period post probe entry. About 100 μL of 1 mg particles (100 nm) in a solution of PBS, $CaCl_2$, $MgCl_2$, and 2% albumin was injected I.V. every hour for 3 hours. The pH was measured continuously throughout.

To determine tumor growth after $CaCO_3$ administration, HT1080 tumors were grown subcutaneously in the dorsal flanks of six athymic nude mice (age ~8-10 weeks). After tumor growth reached about 100 $mm^3$, I.V. treatment with nano-$CaCO_3$ was initiated for three mice. About 1 mg of particles (100 nm) in 100 μL of a solution consisting of PBS, $CaCl_2$, $MgCl_2$, and 20 mg/mL of albumin was injected I.V. every 24 hours for 5 days in three mice. The tumor size was measured for each day concurrently between treated and control for 12 days. The pH in the tumor region was then measured for each mouse as described above. During analysis, tumors that were considered too small to measure but deemed palpable, were assigned the largest size measured on Day 1 (50 mm3) as a conservative estimate.

To determine nonspecific toxicity in rats, 3 month old Sprig Dawley rats (n=3) were injected with an allometrically dosed 25.4 mg/Kg (to match the dose originally given to mice) of 30 mg/mL 100 nm $CaCO_3$ particles in 2% rat serum albumin PBS supplemented with $CaCl_2$ and $MgCl_2$. For controls, 3 month old Sprig Dawley rats (n=3) were injected with a vector of 2% rat serum albumin PBS supplemented with $CaCl_2$ and $MgCl_2$ at an equivalent volume dosage as in the treated group.

Figures 9A, 9B, 9C, 9D:
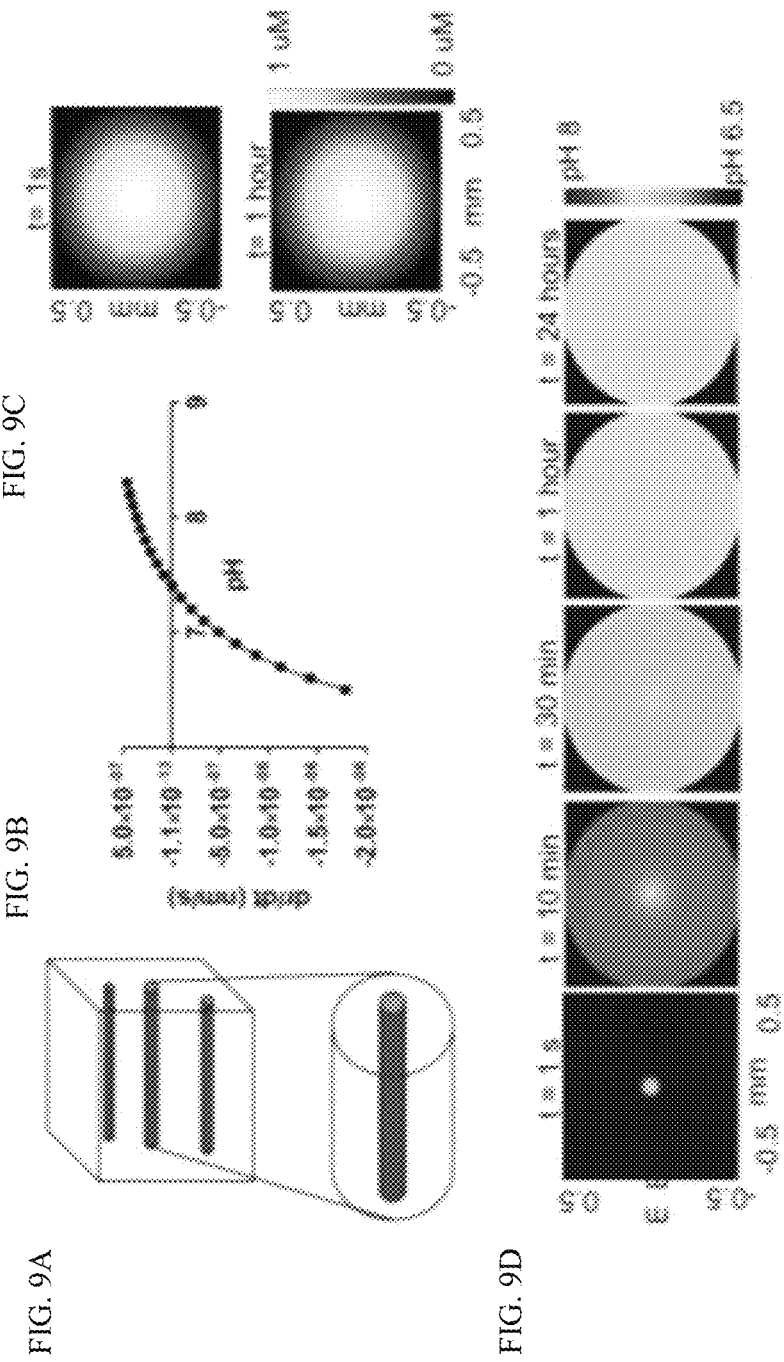
FIG. 9A depicts tissue simulation as a series of cylindrical capillaries each supplying a larger cylindrical volume of tissue for simulation of $CaCO_3$ dissolution in vivo to predict tumor pHe.
FIG. 9B is a graph depicting the rate of change in size of $CaCO_3$ particle reaches an equilibrium at pH=7.4 under in vivo conditions.
FIG. 9C is a heat map depicting the simulated distribution of 100 nm $CaCO_3$ nanoparticles in a circular cross section that reaches ~0.5 mm away from the capillary with constant infusion and degrades minimally over 60 minutes. The capillary source is represented by blue circle.
FIG. 9D depicts the increase in spatial pH distribution over time from 6.5 to 7.4 by 60 minutes, and remains at 7.4 for at least 24 hours. The capillary source is represented by blue circle.

To visualize the $CaCO_3$ dissolution process in a 3D model, nano-$CaCO_3$ diffusion was modeled in a tissue matrix using a tissue cylinder model (FIG. 9A), where a single capillary was assumed to feed a tissue cylinder. The distribution of 100 nm $CaCO_3$ nanoparticles in a circular cross section was simulated to reach ~0.5 mm away from the capillary with constant infusion and degraded minimally over 60 minutes. Rate of change in size of $CaCO_3$ particle reached an equilibrium at pH=7.4 under in vivo conditions. As indicated by the rate of change in size of $CaCO_3$ particles, an equilibration point occurred at a pH of 7.4 (FIG. 9B). This suggested that $CaCO_3$ would only increase pH in acidic environments such as those found in the pHe of solid tumors and that this process is unlikely to induce metabolic alkalosis because the pH would not exceed 7.4. The $CaCO_3$ concentrations were relatively constant over time, predicting a particularly slow dissolution process (FIG. 9C). In addition, the simulation predicted that the pH did not exceed its maximum of 7.4 by 24 hours (FIG. 9D).

$CaCO_3$ nanoparticles that are stable in aqueous solutions have been difficult to synthesize at sub-micron sizes without the use of harsh conditions (custom high pressure systems), doping materials (lipid-based surfactants), other additives such as phosphate, polystyrene, and drugs, or a combination of calcium phosphate and calcium carbonate. Furthermore, $CaCO_3$ nanoparticles can rapidly grow to larger crystalline polymorphs (calcite, vaterite, or aragonite) when placed under aqueous conditions via a variety of mechanisms.

Two independent methods to produce pristine sub-micron vaterite nano-$CaCO_3$ with distinct size ranges at 20 nm, 100 nm, and 300 nm were developed. Synthesis of the 100 nm nano-$CaCO_3$ was accomplished by using a gas diffusion method. The stepwise approach of exposing calcium chloride in anhydrous ethanol to controlled amounts of ammonium bicarbonate, followed by gradual air drying of the product, afforded a simple and highly reproducible method to prepare these nanoparticles. To provide flexibility in particle size, a double decomposition reaction method was used between hydrated calcium chloride and sodium bicarbonate at room temperature. Size control was achieved by mixing the reactants in a mixture of solvents consisting of 1:5 ratio of water/polyethylene glycol (20 nm nano-$CaCO_3$) and water/ethylene glycol (300 nm nano-$CaCO_3$). The ethylene glycol and polyethylene glycol were used to modulate the diffusion rate of calcium and carbonate ions, thereby controlling nucleation and growth by particle cluster formation. This approach revealed that solvent viscosity served as a modular strategy to prepare substantially pure vaterite nanoparticles.

The size and morphology of synthesized nano-$CaCO_3$ were determined by transmission electron microscopy (TEM) and dynamic light scattering (DLS) (FIG. 10). TEM micrographs revealed that nano-$CaCO_3$ were primarily spherical, as expected for vaterite. The geometric mean diameters of the nano-$CaCO_3$ were 20±1.4 nm, 100±8.3 nm and 300±14.6 nm (FIGS. 10A-10C). DLS revealed a slight increase in the hydrodynamic diameter (Dh) for all particle sizes because of the interaction of solvent molecules with the surface of particles, creating a thin layer of solvent molecules (FIG. 10D). Two peaks were observed in the DLS profile of the 20 nm nanoparticles, in which one peak exhibited smaller Dh than the physical diameter. These peaks could arise from the asymmetric shape of the particles, as shown in the 20 nm nano-$CaCO_3$ particles (FIG. 10A). Larger sizes were typically spherical, accounting for the lack of a second smaller peak. Irrespective of the synthesis method, all three sizes of the nano-$CaCO_3$ showed peaks at theta angles of 24.8, 27.1, 32.8 and 43.9, which was consistent with the characteristic hexagonal vaterite crystalline structure of $CaCO_3$ (FIG. 10E).

A variety of biologically compatible media were analyzed to determine storage conditions and vectors for intravenous (I.V.) administration of the nano-$CaCO_3$ (FIGS. 11 & 12). DLS analysis showed a rapid increase of the 100 nm vaterite nanoparticles from 100 nm to over 500 nm within a few seconds in saline and in phosphate buffered saline (PBS; FIG. 11A). The observed morphological change in PBS could be attributed to calcite or $CaPO_4$ formation. However, addition of 2% albumin to PBS remarkably stabilized the materials for extended periods, demonstrating the potential of formulating vaterite nanoparticles in this medium for I.V. administration (FIGS. 11A & 11B). A similar trend was observed with the 20 nm and 300 nm nano-$CaCO_3$ (FIG. 12A-12F).

Figure 11A:
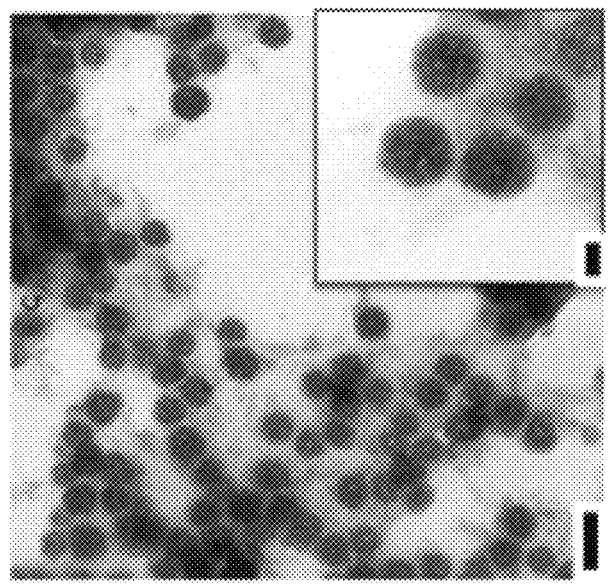
FIG. 11A is a graph of DLS results of 100 nm particles showing that stability in serum>PBS+BSA+$CaCl_2$>PBS+$CaCl_2$>Saline=DI Water>PBS.
Figure 11B:
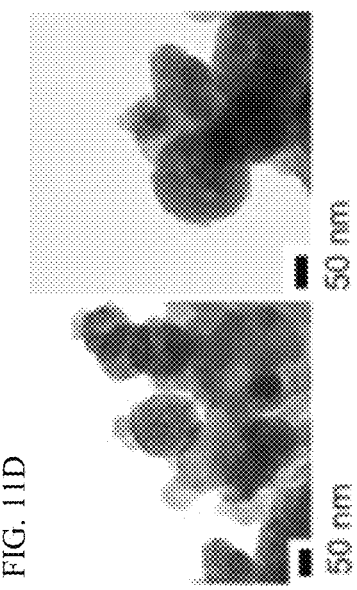
FIG. 11B is a TEM showing 100 nm particles in albumin solution have unchanged morphology surrounded by albumin.
Figure 11C:
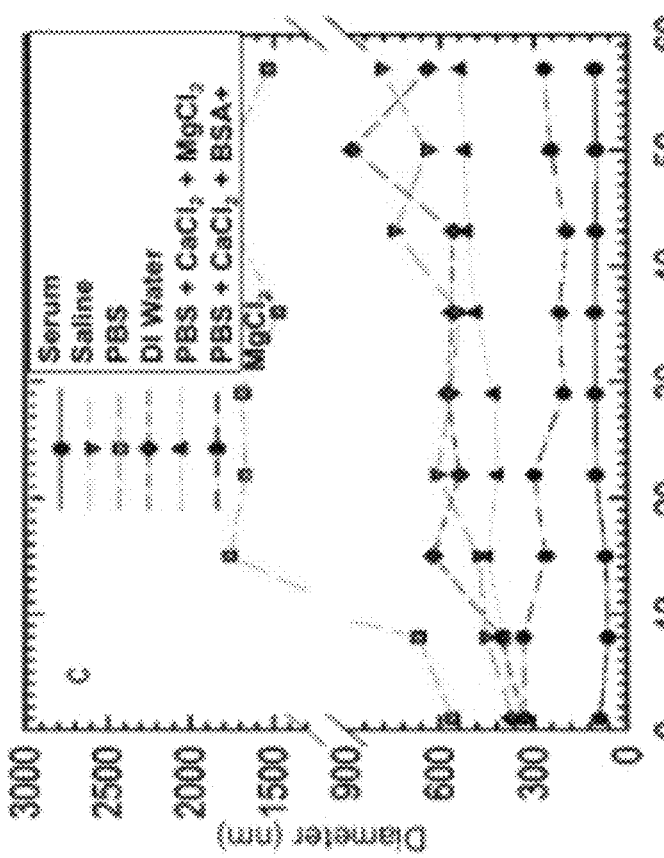
FIG. 11C is a graph depicting XRD of 100 nm particles in albumin solution at 24 hours showing no changes in crystalline structure.
Figure 11D:
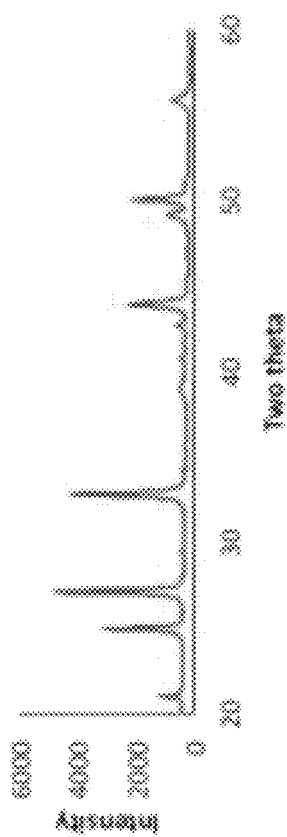
FIG. 11D is a TEM of particles post serum incubation demonstrating no change in structure, with particles embedded in serum protein.

The long-term particle stability was determined in different media for up to 7 hours. Time-resolved DLS (TR-DLS) suggests that the particles in aqueous albumin containing solution exist in pairs of 2 or 3 (size 2-3 times larger than in ethanol), which dissociate into individual particles upon exposure to fetal serum (FIG. 11A & FIG. 12). TEM confirmed the high stability of the particles in albumin solution (FIGS. 11A & 12). X-Ray Diffraction (XRD) analysis did not show any change in crystallinity in albumin-based aqueous media (FIG. 11C). The nano-$CaCO_3$ exhibited stability in both morphology and size in fetal bovine serum (FIG. 11D & FIG. 12).

These results indicate that albumin, which has a high affinity for calcium, serves as a calcium sink that prevents aggregation and calcium phosphate formation in PBS. The minimal change in TEM (structural) and X-ray diffraction (crystalline) analyses confirmed that extensive double replacement to form $CaPO_4$ did not occur. In general, clusters of three nano-$CaCO_3$ formed in albumin solutions, which separated into single particle when serum was added to the mixture. The additional serum stability conferred on nano-$CaCO_3$ in aqueous albumin solution indicates that pre-formulation of the nanoparticles in this medium is ideal for in vivo application, where serum is abundant.

Figure 13B:
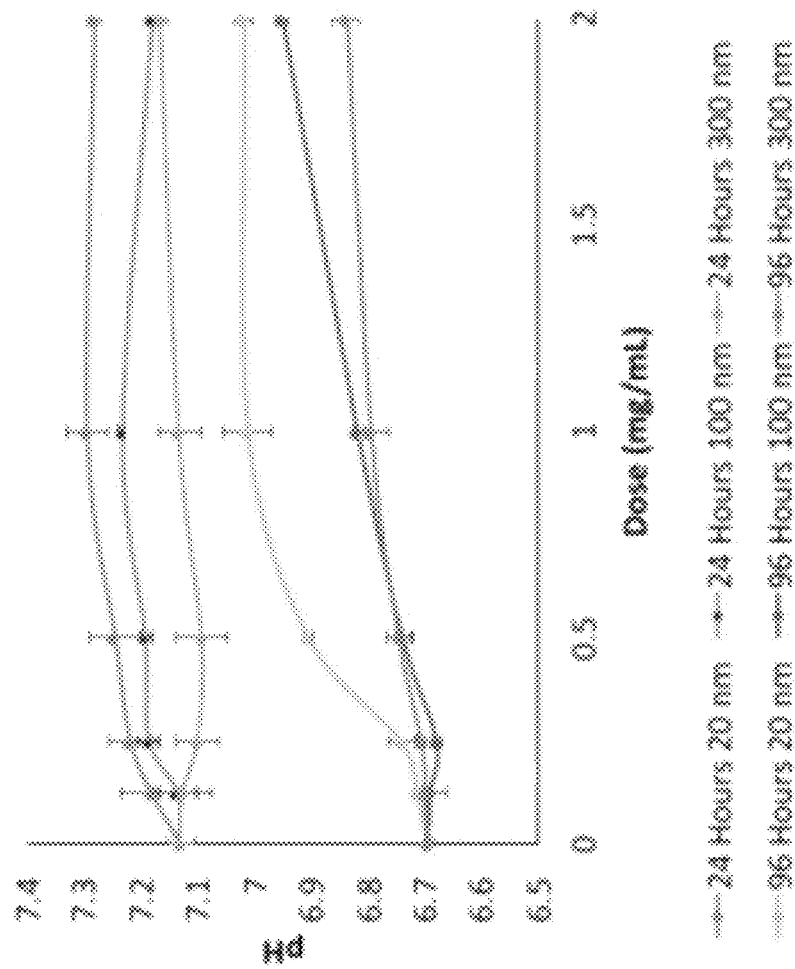
FIG. 13B is a graph depicting pH change versus dose when incubated with HT1080 (human fibrosarcoma) cells using different particle sizes showing an increase in pH with one dose of $CaCO_3$, as well as a differential effect on pH at later time points of growth depending on size. Error bars refer to the standard error across n=3 biologic replicates.
Figure 13A:
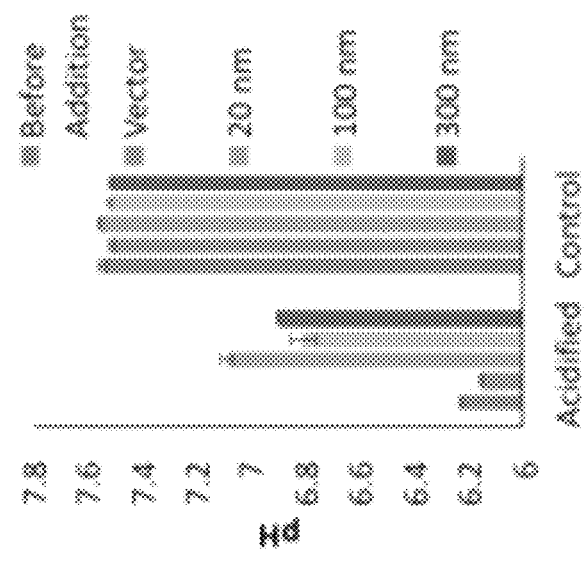
FIG. 13A is a graph of the pH change in media at 5% $CO_2$ depicting a significant increase in pH when using particles as compared to vector alone. All solutions were added in 10 pit solvent (2% albumin+PBS with $CaCl_2$ and $MgCl_2$).
Figure 16A:
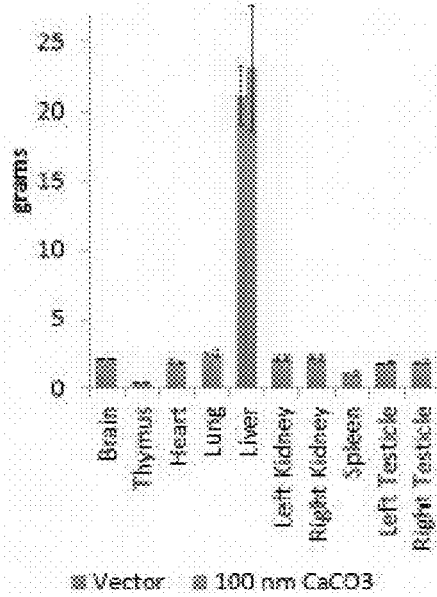
FIG. 16A is a graph depicting organ weights after 24 hours $CaCO_3$ treatment from rats using allometrically dosed $CaCO_3$ for toxicity study.
Figure 16B:
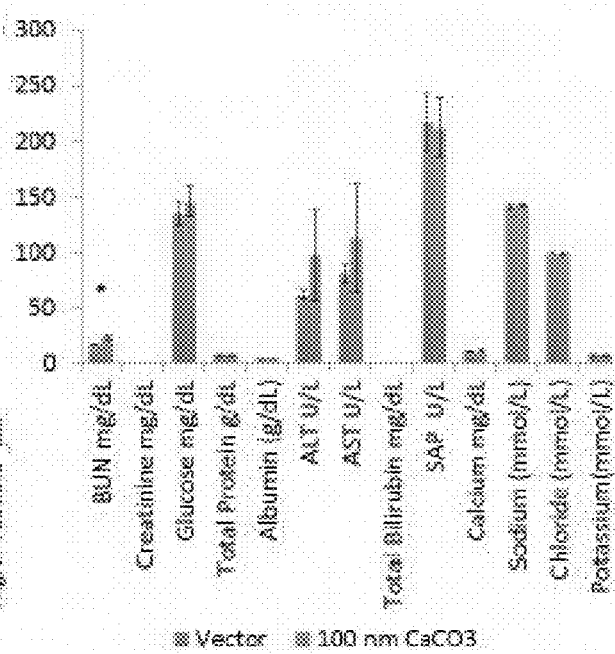
FIG. 16B is a graph depicting chemistry results of blood metabolites after 24 hours from rats using allometrically dosed $CaCO_3$ for toxicity study. * represents $p<0.05$.
Figure 16C:
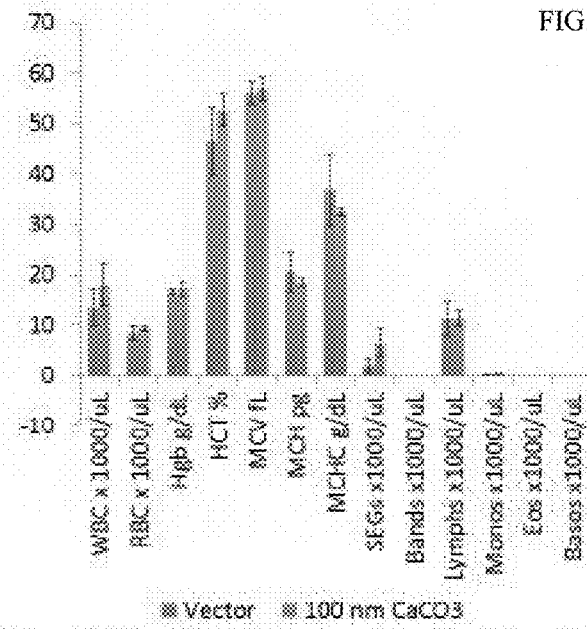
FIG. 16C is a graph depicting complete blood count of cells 24 hours after $CaCO_3$ injection from rats using allometrically dosed $CaCO_3$ for toxicity study.
Figure 16D:
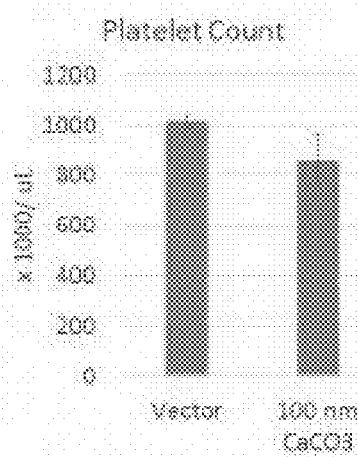
FIG. 16D is a graph depicting platelet count 24 hours after $CaCO_3$ inject from rats using allometrically dosed $CaCO_3$ for toxicity study.

Predicated on the simulation studies, the buffering capacity of the nanoparticles in cell-free media under 5% $CO_2$ and hypoxic (0.3% $O_2$) conditions was assessed (FIG. 13A). In non-acidified conditioned media (pH 7.4), the solution pH was largely unchanged in the presence of different sizes and concentrations of vaterite nano-$CaCO_3$, as predicted by simulations above. However, treatment of acidic conditioned media (pH 6.2) with any of the particles (0.67 mg/mL) showed a rapid increase in pH, which did not exceed 7.2. Similarly, the pH remained at about pH 7.2 after 24 hours incubation of human fibrosarcoma (HT1080) cells in normal cell culture conditions, irrespective of the nanoparticle doses used (FIG. 13B). At 96 hours post-HT1080 cellular induced acidification, nanoparticle size-dependent pH changes were observed, with the 20 nm nano-$CaCO_3$ having the highest increase in pH. Without being bound by theory, this could be attributable to the higher diffusion rate and the larger surface area of the 20 nm nano-$CaCO_3$.

To test whether nano-$CaCO_3$ was capable of increasing pH in vivo, a large 5 mm diameter invasive pH electrode probe was used for determining in vivo pH (FIG. 14A). The large size of the probe was chosen to primarily ensure extracellular pH sampling (cells are on average 10 µm in diameter), and to average across the significant tumor heterogeneity in pH. Based on this technique, a control vector administration resulted in a slight decrease in pH over time, possibly due to cell lysis and inflammation from the probe injury. Against this background, I.V. administration of 1 mg bolus injections of each of the 3 types of nano-$CaCO_3$ in HT1080 tumor-bearing mice increased the tumor pH for over 3 h at varying amounts. The 100 nm nano-$CaCO_3$ particles showed the highest ΔpH and longest effect (FIG. 14B). The 20 nm nano-$CaCO_3$ particles appeared to diffuse into and out of the tumor area more rapidly than the 100 nm particles. The 300 nm nano-$CaCO_3$ particles did not appear to appreciably increase the pHe of tumors. The poor diffusion of these particles dictates that they can only exert an effect in a small section of a three dimensional tumor environment. Data also showed that flooding the mouse with a high concentration (0.3-0.4 g/Kg) of sodium bicarbonate (~10× the nanoparticle I.V. dosage) did not induce a measurable pH change in the tumor region (FIG. 14B), which may be due to rapid clearing by the kidney and lungs.

Dynamic pH measurements in mice bearing HT1080 tumors indicated that 100 nm sized nano-$CaCO_3$ particles administered at a bolus dose of 1 mg (0.04-0.05 g/kg body weight) almost linearly increased the pH during the first 30 minutes, followed by a decrease at about 100 minutes. Repeated dosing at selected time points maintained the pH close to 7.4 (FIG. 14C), which matched the expectations of the simulation (FIG. 9). Repeated daily administration of nano-$CaCO_3$ particles significantly inhibited tumor growth (FIGS. 15A & 15B). Further, discontinuation of the nano-CaCO₃ particle treatment partially reversed this trend, resulting in the acceleration of tumor growth rate (FIGS. 15C & 15D). This finding suggests that the potential of tumor cell reprogramming in response to an initial assault by nano-CaCO₃ particles.

A rat animal model was used for translational toxicity studies. CaCO₃ should not increase the pH beyond the normal 7.4 in other tissues. Otherwise, significant toxicity in organs such as the liver, kidney, or spleen would be expected. In addition, there are certain parts of the kidney and stomach that are generally more acidic than usual due to hypoxic stress or for digestion. Here the model would expect some rising of pH to 7.4, although it is unclear whether this would induce downstream toxicity.

Little to no significant changes in organ weights, blood chemistries, and blood counts was observed 24 hours after nano-CaCO₃ particle injection compared to control. (FIG. 16A-16D). There was a significant albeit slight rise in blood urea nitrogen, but because there was no concurrent creatinine or liver enzyme rise, the rise was suggested to be nonspecific. There was nonspecific histologic level pathology across both control and treated groups, which was attributed to age. These results indicated that nano-CaCO₃ particles did not induce widespread toxicity, which is likely due to the pH not increasing beyond 7.4 in normal organs.

The results presented herein provide a facile, scalable method for mass production of sub-micron vaterite calcium carbonate nanoparticles that are stable in biological media. Two different methods wherein particle nucleation and cluster growth could be effectively controlled were demonstrated to obtain the desired size ranges and crystal phases of calcium carbonate nanoparticles. The results also demonstrated the capability of modulating the pHe in vivo of solid tumors using nano-CaCO₃ particles.

What is claimed is:

1. A calcium carbonate nanoparticle comprising a calcium carbonate nanoparticle, an amino functionalized silica coating and a pH low insertion (pHLI) peptide, wherein the pH low insertion (pHLI) peptide N-terminus is coupled to the silica coating.

2. The calcium carbonate nanoparticle of claim 1, wherein the pH low insertion peptide (pHLI) comprises an extracellular amino (N-) terminus of pH low insertion peptide (pHLI).

3. The calcium carbonate nanoparticle of claim 1, further comprising a therapeutic agent coupled to the pH low insertion (pHLI) peptide C-terminus.

4. The calcium carbonate nanoparticle of claim 3, wherein the therapeutic agent is a cytotoxic agent.

5. The calcium carbonate nanoparticle of claim 1, further comprising a pH-sensitive dye coupled to the pH low insertion (pHLI) peptide C-terminus.

6. The calcium carbonate nanoparticle of claim 5, wherein the dye is LS662.

7. The calcium carbonate nanoparticle of claim 1, wherein the calcium carbonate nanoparticle comprises a diameter of about 20 nm to about 500 nm.

* * * * *

```
                        SEQUENCE LISTING

<160> NUMBER OF SEQ ID NOS: 4

<210> SEQ ID NO 1
<211> LENGTH: 37
<212> TYPE: PRT
<213> ORGANISM: Artificial Sequence
<220> FEATURE:
<223> OTHER INFORMATION: Synthetic

<400> SEQUENCE: 1

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Gly
        35

<210> SEQ ID NO 2
<211> LENGTH: 37
<212> TYPE: PRT
<213> ORGANISM: Artificial Sequence
<220> FEATURE:
<223> OTHER INFORMATION: Synthetic

<400> SEQUENCE: 2

Ala Cys Glu Gln Asn Pro Ile Tyr Trp Ala Arg Tyr Ala Lys Trp Leu
1               5                   10                  15

Phe Thr Thr Pro Leu Leu Leu Leu Lys Leu Ala Leu Leu Val Asp Ala
            20                  25                  30

Asp Glu Gly Thr Gly
        35

<210> SEQ ID NO 3
<211> LENGTH: 38
<212> TYPE: PRT
<213> ORGANISM: Artificial Sequence
<220> FEATURE:
<223> OTHER INFORMATION: Synthetic

<400> SEQUENCE: 3

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30
```

```
Asp Glu Gly Thr Gly Lys
        35

<210> SEQ ID NO 4
<211> LENGTH: 38
<212> TYPE: PRT
<213> ORGANISM: Artificial Sequence
<220> FEATURE:
<223> OTHER INFORMATION: Synthetic

<400> SEQUENCE: 4

Ala Cys Glu Gln Asn Pro Ile Tyr Trp Ala Arg Tyr Ala Lys Trp Leu
1               5                   10                  15

Phe Thr Thr Pro Leu Leu Leu Leu Lys Leu Ala Leu Leu Val Asp Ala
            20                  25                  30

Asp Glu Gly Thr Gly Lys
        35
```